(12) United States Patent
Roussel et al.

(10) Patent No.: US 6,245,965 B1
(45) Date of Patent: Jun. 12, 2001

(54) KNOCKOUT MICE AND CELLS THAT LACK P19$^{INK4D}$ AND P27$^{KIP1}$ ACTIVITY AND METHODS OF USE THEREOF

(75) Inventors: Martine F. Roussel, Memphis; Richard Smeyne, Collierville; Frederique Zindy; Justine Cunningham, both of Memphis, all of TN (US)

(73) Assignee: St. Jude Children's Research Hospital, Memphis, TN (US)

( * ) Notice: Subject to any disclaimer, the term of this patent is extended or adjusted under 35 U.S.C. 154(b) by 0 days.

(21) Appl. No.: 09/240,906

(22) Filed: Jan. 29, 1999

(51) Int. Cl.⁷ .......................... G01N 33/00; A01K 67/00; C12N 15/85; C12N 15/86
(52) U.S. Cl. ................................ 800/18; 800/3; 800/8; 800/13; 800/14; 435/325
(58) Field of Search ................................ 800/3, 8, 9, 14, 800/18, 21, 22, 13; 435/325

(56) References Cited

PUBLICATIONS

Mullins et al. J. Clin. Invest., vol. 98, pp. S37–S40, 1996.*
Moreadith et al, J. Mol. Med., vol. 75, pp. 208–216, 1997.*
Wall Theriogenology, vol. 45, pp. 57–68, 1996.*
Zindy et al., Cell Growth and Diff., vol. 8, pp. 1139–1150, Nov. 1997.*
Brotherton et al., 1998, Nature 395:244–250.
Casaccia–Bonnefil et al., 1997, Genes Dev. 11:2335–46.
Chen et al., 1999, PNAS Development, 126:1581–90.
Fero et al., 1998, Nature 396:177.
Fero et al., 1996, Cell 85:733–744.
Franklin et al., 1998, Genes Dev. 12:2899–2911.
Freed et al., 1992, New England J. Med. 327:1549–55.
Harper et al., 1996, Curr. Opin. Genet. Dev. 6:56–64.
Kiyokawa et al., 1996, Cell 85:721–32.
Lee et al., 1996, PNAS 93:3259.
Lowenheim et al., 1999, PNAS, 30:4084–88.
Nakayama et al., 1996, Cell 85:707–720.
Sherr, 1993, Cell 73:1059–1065.
Sherr et al., 1995, Gene Dev. 9:1149–63.
Thomas et al., 1996, Glia 17:1–14 (Abs).
Vicario–Abejon et al., 1995, Neuron 15:105–114.
Zhang et al., 1998, Genes Dev. 12:3162–3167.
Zhang et al., 1999, Exp. Neurol 155:140–49 (Abs).
Zhang et al., 1997, Nature 387:151–158.
Zindy et al., 1997, Cell Growth & Differ 8:1139–50.

* cited by examiner

*Primary Examiner*—Deborah J. R. Clark
*Assistant Examiner*—Michael C. Wilson
(74) *Attorney, Agent, or Firm*—Klauber & Jackson

(57) ABSTRACT

Non-human animals that have been manipulated so as not to express a functional p19$^{INK4d}$ and p27$^{KIP1}$ proteins are described. One particulat non-human animal exemplified is a p19$^{INK4d}$-double null, p27$^{KIP1}$-double null mouse. Such knockout mice exhibit bradykinesia, proprioceptive abnormalties, seizure-like activity, and generally die 14–24 days after birth. In addition, mammalian cells having the p19$^{INK4d}$-double null, p27$^{KIP1}$-double null genotype are characterized. Methods of making and using the non-human knockout animals and cells are disclosed.

7 Claims, 5 Drawing Sheets

SEQUENCE LISTING

<160> NUMBER OF SEQ ID NOS: 8

<210> SEQ ID NO 1
<211> LENGTH: 555
<212> TYPE: DNA
<213> ORGANISM: Homo sapiens

<400> SEQUENCE: 1

```
tgacagcgcc gggctgggc ggggcggggg gctttgcagg ccgccagtgt cgacatgctg      60
ctggaggagg ttcgcgccgg cgaccggctg agtgggcg cggcccgggg cgacgtgcag     120
gaggtgcgcc gccttctgca ccgcgagctg gtgcatcccg acgccctcaa ccgcttcggc     180
aagacggcgc tgcaggtcat gatgtttggc agcaccgcca tcgccctgga gctgctgaag     240
caaggtgcca gccccaatgt ccaggacacc tccggtacca gtccagtcca tgacgcagcc     300
cgcactggat tcctggacac cctgaaggtc ctagtggagc acggggctga tgtcaacgtg     360
cctgatggca ccggggcact tccaatccat ctggcagttc aagagggtca cactgctgtg     420
gtcagctttc tggcagctga atctgatctc catcgcaggg acgccagggg tctcacaccc     480
ttggagctgg cactgcagag agggctcag gacctcgtgg acatcctgca gggccacatg     540
gtggccccgc tgtga                                                     555
```

<210> SEQ ID NO 2
<211> LENGTH: 166
<212> TYPE: PRT
<213> ORGANISM: Homo sapiens

<400> SEQUENCE: 2

```
Met Leu Leu Glu Glu Val Arg Ala Gly Asp Arg Leu Ser Gly Ala Ala
 1               5                  10                  15

Ala Arg Gly Asp Val Gln Glu Val Arg Arg Leu Leu His Arg Glu Leu
            20                  25                  30

Val His Pro Asp Ala Leu Asn Arg Phe Gly Lys Thr Ala Leu Gln Val
        35                  40                  45

Met Met Phe Gly Ser Thr Ala Ile Ala Leu Glu Leu Leu Lys Gln Gly
    50                  55                  60

Ala Ser Pro Asn Val Gln Asp Thr Ser Gly Thr Ser Pro Val His Asp
65                  70                  75                  80

Ala Ala Arg Thr Gly Phe Leu Asp Thr Leu Lys Val Leu Val Glu His
                85                  90                  95

Gly Ala Asp Val Asn Val Pro Asp Gly Thr Gly Ala Leu Pro Ile His
            100                 105                 110

Leu Ala Val Gln Glu Gly His Thr Ala Val Val Ser Phe Leu Ala Ala
        115                 120                 125

Glu Ser Asp Leu His Arg Arg Asp Ala Arg Gly Leu Thr Pro Leu Glu
    130                 135                 140
```

```
Leu Ala Leu Gln Arg Gly Ala Gln Asp Leu Val Asp Ile Leu Gln Gly
145                 150                 155                 160

His Met Val Ala Pro Leu
                165
```

<210> SEQ ID NO 3
<211> LENGTH: 941
<212> TYPE: DNA
<213> ORGANISM: Mus musculus

<400> SEQUENCE: 3

```
cgaattcggc acgagagttg gccctggtgg caccgcagtc cctagagttc tgatccagct     60
cttgctggtt ccccagccct gaccttaact gggcttgggg ctgggtgggt ttcacagtcc    120
accggtatcc actatgcttc tggaagaagt ctgcgtcggc gaccggttga gtggcgcacg    180
ggcccgtggc gacgtgcaag aggtccgccg ccttcttcac cgggagctgg tgcatcctga    240
cgccctgaac cgctttggca agacggcctt gcaggtcatg atgtttggaa gtccagcagt    300
tgctttggag ctcctgaagc aaggtgccag ccccaatgtc caagatgcct ccggtactag    360
tcctgtgcat gatgcggctc gcaccgggtt cctggacacc ctgaaggttc tggtggagca    420
tggtgctgat gtcaatgccc tggacagcac tgggtcgctc cccatccatc tggcgataag    480
agagggccat agctccgtgg tcagcttcct agctcctgaa tctgatctcc accacaggga    540
cgcttccggt ctcactcccc tggagttggc tcggcagaga ggggctcaga acctcatgga    600
cattctgcag ggcacatga tgatcccaat gtgacccaag ccactgtct ccagccttac     660
tgggttactt gtcaacaaaa gaggaaagaa actttctctt ttcacacctg tccattgaag    720
aagggagtgg gaggagcagt ttgtggttta ttggtgttga tttcttgagt gtgtgtgttt    780
gggggtgtt tctcatttgt ttttcctcac ccctttgggt gtgttggaaa agaagggtcc     840
tacaggcaac agatctaaat ggttcagttt cctctgcact ggggctgcac cagggcaggg    900
gttaaagccc tagcctcaga gtgaggtcat cacttcccgg g                        941
```

<210> SEQ ID NO 4
<211> LENGTH: 166
<212> TYPE: PRT
<213> ORGANISM: Mus musculus

<400> SEQUENCE: 4

```
Met Leu Leu Glu Glu Val Cys Val Gly Asp Arg Leu Ser Gly Ala Arg
  1               5                  10                  15

Ala Arg Gly Asp Val Gln Glu Val Arg Arg Leu Leu His Arg Glu Leu
                 20                  25                  30

Val His Pro Asp Ala Leu Asn Arg Phe Gly Lys Thr Ala Leu Gln Val
         35                  40                  45

Met Met Phe Gly Ser Pro Ala Val Ala Leu Glu Leu Leu Lys Gln Gly
     50                  55                  60

Ala Ser Pro Asn Val Gln Asp Ala Ser Gly Thr Ser Pro Val His Asp
 65                  70                  75                  80

Ala Ala Arg Thr Gly Phe Leu Asp Thr Leu Lys Val Leu Val Glu His
                 85                  90                  95

Gly Ala Asp Val Asn Ala Leu Asp Ser Thr Gly Ser Leu Pro Ile His
```

```
                    100                 105                 110
Leu Ala Ile Arg Glu Gly His Ser Ser Val Val Ser Phe Leu Ala Pro
            115                 120                 125

Glu Ser Asp Leu His His Arg Asp Ala Ser Gly Leu Thr Pro Leu Glu
        130                 135                 140

Leu Ala Arg Gln Arg Gly Ala Gln Asn Leu Met Asp Ile Leu Gln Gly
145                 150                 155                 160

His Met Met Ile Pro Met
                165

<210> SEQ ID NO 5
<211> LENGTH: 597
<212> TYPE: DNA
<213> ORGANISM: Homo sapiens

<400> SEQUENCE: 5
atgtcaaacg tgcgagtgtc taacgggagc cctagcctgg agcggatgga cgccaggcag      60
gcggagcacc ccaagccctc ggcctgcagg aacctcttcg gcccggtgga ccacgaagag     120
ttaacccggg acttggagaa gcactgcaga gacatggaag aggcgagcca gcgcaagtgg     180
aatttcgatt ttcagaatca caaaccccta gagggcaagt acgagtggca agaggtggag     240
aagggcagct tgcccgagtt ctactacaga ccccgcggc cccccaaagg tgcctgcaag      300
gtgccggcgc aggagagcca ggatgtcagc gggagccgcc cggcggcgcc tttaattggg     360
gctccggcta actctgagga cacgcatttg gtggacccaa agactgatcc gtcggacagc     420 cagacgggt tagcggagca atgcgcagga ataaggaagc gacctgcaac cgacgattct      480
tctactcaaa acaaaagagc caacagaaca gaagaaaatg tttcagacgg ttccccaaat    540
gccggttctg tggagcagac gcccaagaag cctggcctca gaagacgtca aacgtaa       597

<210> SEQ ID NO 6
<211> LENGTH: 198
<212> TYPE: PRT
<213> ORGANISM: Homo sapiens

<400> SEQUENCE: 6

Met Ser Asn Val Arg Val Ser Asn Gly Ser Pro Ser Leu Glu Arg Met
1               5                   10                  15

Asp Ala Arg Gln Ala Glu His Pro Lys Pro Ser Ala Cys Arg Asn Leu
            20                  25                  30

Phe Gly Pro Val Asp His Glu Glu Leu Thr Arg Asp Leu Glu Lys His
        35                  40                  45

Cys Arg Asp Met Glu Glu Ala Ser Gln Arg Lys Trp Asn Phe Asp Phe
    50                  55                  60

Gln Asn His Lys Pro Leu Glu Gly Lys Tyr Glu Trp Gln Glu Val Glu
65                  70                  75                  80

Lys Gly Ser Leu Pro Glu Phe Tyr Tyr Arg Pro Pro Arg Pro Pro Lys
                85                  90                  95

Gly Ala Cys Lys Val Pro Ala Gln Glu Ser Gln Asp Val Ser Gly Ser
            100                 105                 110

Arg Pro Ala Ala Pro Leu Ile Gly Ala Pro Ala Asn Ser Glu Asp Thr
        115                 120                 125

His Leu Val Asp Pro Lys Thr Asp Pro Ser Asp Ser Gln Thr Gly Leu
    130                 135                 140

Ala Glu Gln Cys Ala Gly Ile Arg Lys Arg Pro Ala Thr Asp Asp Ser
145                 150                 155                 160
```

Ser Thr Gln Asn Lys Arg Ala Asn Arg Thr Glu Glu Asn Val Ser Asp
                165                 170                 175

Gly Ser Pro Asn Ala Gly Ser Val Glu Gln Thr Pro Lys Lys Pro Gly
            180                 185                 190

Leu Arg Arg Arg Gln Thr
        195

<210> SEQ ID NO 7
<211> LENGTH: 594
<212> TYPE: DNA
<213> ORGANISM: Mus musculus

<400> SEQUENCE: 7
atgtcaaacg tgagagtgtc taacgggagc ccgagcctgg agcggatgga cgccagacaa     60
gcggatcacc ccaagccttc cgcctgcaga atctcttcg gcccggtcaa tcatgaagaa     120
ctaacccggg acttggagaa gcactgccgg gatatggaag aagcgagtca gcgcaagtgg     180
aatttcgact tcagaatca taagcccctg gagggcagat acgaatggca ggaggtggag     240
aggggcagct tgcccgagtt ctactacagg ccccgcgcc cccaagag cgcctgcaag      300 gtgctggcgc aggagagcca ggatgtcagc gggagccgcc aggcggtgcc tttaattggg     360
tctcaggcaa actctgagga ccggcatttg gtggaccaaa tgcctgactc gtcagacaat     420
caggctgggt tagcggagca gtgtccaggg atgaggaagc gacctgctgc agaagattct     480
tcttcgcaaa acaaaaggc caacagaaca gaagaaaatg tttcagacgg ttcccccgaac    540 gctggcactg tggagcagac gcccaagaag cccggccttc gacgccagac gtaa          594

<210> SEQ ID NO 8
<211> LENGTH: 197
<212> TYPE: PRT
<213> ORGANISM: Mus musculus

<400> SEQUENCE: 8

Met Ser Asn Val Arg Val Ser Asn Gly Ser Pro Ser Leu Glu Arg Met
 1               5                  10                  15

Asp Ala Arg Gln Ala Asp His Pro Lys Pro Ser Ala Cys Arg Asn Leu
             20                  25                  30

Phe Gly Pro Val Asn His Glu Glu Leu Thr Arg Asp Leu Glu Lys His
         35                  40                  45

Cys Arg Asp Met Glu Glu Ala Ser Gln Arg Lys Trp Asn Phe Asp Phe
     50                  55                  60

Gln Asn His Lys Pro Leu Glu Gly Arg Tyr Glu Trp Gln Glu Val Glu
 65                  70                  75                  80

Arg Gly Ser Leu Pro Glu Phe Tyr Tyr Arg Pro Pro Arg Pro Pro Lys
                 85                  90                  95

Ser Ala Cys Lys Val Leu Ala Gln Glu Ser Gln Asp Val Ser Gly Ser
            100                 105                 110

Arg Gln Ala Val Pro Leu Ile Gly Ser Gln Ala Asn Ser Glu Asp Arg
        115                 120                 125

His Leu Val Asp Gln Met Pro Asp Ser Ser Asp Asn Gln Ala Gly Leu
    130                 135                 140

Ala Glu Gln Cys Pro Gly Met Arg Lys Arg Pro Ala Ala Glu Asp Ser
145                 150                 155                 160

Ser Ser Gln Asn Lys Arg Ala Asn Arg Thr Glu Glu Asn Val Ser Asp
                165                 170                 175

-continued

```
Gly Ser Pro Asn Ala Gly Thr Val Glu Gln Thr Pro Lys Lys Pro Gly
            180                 185                 190

Leu Arg Arg Gln Thr
        195
```

KNOCKOUT MICE AND CELLS THAT LACK P19$^{INK4D}$ AND P27$^{KIP1}$ ACTIVITY AND METHODS OF USE THEREOF

RESEARCH SUPPORT

The research leading to the present invention was supported in part by a grant from the NIH, Grant No. CA-71907 and Cancer Center Core Grant CA-21765 from the National Cancer Institute. Accordingly the government may have certain rights in the present invention. Support for this invention was also provided by the AMERICAN LEBANESE SYRIAN ASSOCIATED CHARITIES (ALSAC) of St. Jude Children's Research Hospital.

FIELD OF THE INVENTION

The present invention is directed towards specific knockout animals and their use as animal models. More specifically, the knockout animals contain a disruption in the genes encoding p19$^{INK4d}$ and p27$^{KIP1}$. Corresponding cells which are amenable to tissue culture are also part of the invention, as are methods of using such cells, including their use as a potential source of differentiated neuronal cells.

BACKGROUND OF THE INVENTION

The cell cycle for growing cells can be divided into two periods: (1) the cell division period, when the cell divides and separates, with each daughter cell receiving identical copies of the DNA; and (2) the period of growth, known as the interphase period. For the cell cycle of eucaryotes, the cell division period is labeled the M (mitotic) period. The interphase period in eucaryotes is further divided into three successive phases: G1 (gap 1) phase, which directly follows the M period; S (DNA synthetic) phase, which follows G1; and G2 (gap 2) phase, which follows the S phase, and immediately precedes the M period. During the two gap phases no net change in DNA occurs, though damaged DNA may be repaired. On the other hand, throughout the interphase period there is continued cellular growth and continued synthesis of other cellular components. Towards the end of the G1 phase, the cell passes a restrictive (R) point and becomes committed to duplicate its DNA. At this point, the cell is also committed to divide. During the S phase, the cell replicates DNA. The net result is that during the G2 phase, the cell contains two copies of all of the DNA present in the G1 phase. During the subsequent M period, the cells divide with each daughter cell receiving identical copies of the DNA. Each daughter cell starts the next round of the growth cycle by entering the G1 phase.

The G1 phase represents the interval in which cells respond maximally to extracellular signals, including mitogens, anti-proliferative factors, matrix adhesive substances, and intercellular contacts. Passage through the R point late in G1 phase defines the time at which cells lose their dependency on mitogenic growth factors for their subsequent passage through the cycle and, conversely, become insensitive to anti-proliferative signals induced by compounds such as transforming growth factor, cyclic AMP analogs, and rapamycin. Once past the R point, cells become committed to duplicating their DNA and to undergoing mitosis, as noted above, and the programs governing these processes are largely cell autonomous.

In mammalian cells, a molecular event that temporally coincides with passage through the R point is the phosphorylation of the retinoblastoma protein (Rb). In its hypophosphorylated state, Rb prevents the cell from exiting the G1 phase by combining with transcription factors such as E2F to actively repress transcription from promoters containing E2F binding sites. However, hyperphosphlorylation of Rb late in G1 phase prevents its interaction with E2F, thus allowing E2F to activate transcription of the same target genes. As many E2F-regulated genes encode proteins that are essential for DNA synthesis, Rb phosphorylation at the R point helps convert cells to a pre-replicative state that anticipates the actual G1/S transition by several hours.

Regulation of the human cell cycle requires the periodic formation, activation, and inactivation of protein kinase complexes that consist of a regulatory "cyclin" subunit and a catalytic "cyclin dependent kinase" (CDK) subunit. Cell cycle-dependent fluctuations in the levels of many of the cyclin proteins contribute to the activation of these protein kinase complexes. For example, cyclin B participates in the regulation of the G2/M transition by its association with its catalytic subunit, p34$^{cdc2}$, whereas cyclin A, in complexes with both p34$^{cdc2}$ and CDK2, is essential for the completion of S-phase and entry into G2-phase. Complexes formed between the D-type cyclins and either CDK4 or CDK6 integrate growth factor signals and the cell cycle, allowing cells to progress through G1-phase. This particular cell cycle pathway is specifically altered during tumorigenesis, presumably due to its role in responses to mitogenic stimulation. Alterations have been identified in many components of this pathway, including the D-type cyclins, CDKs, and cyclin dependent kinase inhibitors (CKIs). Another G1-phase cyclin, cyclin E, in conjunction with its catalytic subunit CDK2, appears to be essential for progression from G1-phase into S-phase and the initiation of DNA replication. Cyclin E and CDK2 do not appear to be directly targeted during tumorigenesis, quite possibly due to their essential nature. [See generally, Sherr, Cell 73:1059–1065 (1993), and Sherr, Cell 79:551–555 (1994)].

A class of novel polypeptides that are collectively known as CDK inhibitors (CKIs) can negatively regulate cyclin/CDK activity by associating with these complexes. These so-called "cell cycle brakes" act to inhibit cyclin/CDK complexes by binding specifically to either CDK, (i.e.,the INK4s, see below) or the cyclin/CDK complexes (i.e., KIP1/CIP1, see below). CKI activity and levels are cell cycle regulated allowing these proteins to function as inhibitors of their cognate cyclin/CDK complexes for very limited periods during the cell cycle, There are two types of CKIs that have been identified, the INK4s, and the CIP/KIPs [Sherr & Roberts, Genies Devel. 9:1149–1163 (1995)]. The INK4 family of inhibitors comprises four members, p16$^{INK4a}$, p15$^{INK4b}$, p18$^{INK4c}$ and p19$^{INK4d}$, which specifically bind to and inhibit G1-specific CDK4 and CDK6, and thereby prevent phosphorylation of the retinoblastoma (Rb) protein and S phase entry. The CIP/KIP family of inhibitors includes p21$^{CIP1}$, p27$^{KIP1}$, and p57$^{KIP2}$, and unlike the INK4 proteins, can inhibit all cyclin/CDK complexes [Harper & Elledge, Curr. Opin. Genet. Dev. 6:56–64 (1996)]. This apparent redundancy in CDK complex inhibitors has been explained as a method for organisms to govern transitions through the R point in different cell types responding to a plethora of distinct extracellular signals.

Despite their apparent biochemical redundancy, the CKIs are differentially expressed during mammalian (e.g., mouse) development and in adult tissues, showing some overlapping expression patterns. Deletion of a single CKI or in combination with another in the mouse leads to specific phenotypes, but in spite of their reported expression in the central nervous system (CNS) none give rise to a reported phenotype in the brain. For example, mice lacking p57$^{KIP2}$, die soon after birth and display developmental defects mimicking those observed in human patients with Beckwith-Weideman syndrome [Zhang et al., *Nature* 387:151–158 (1997); Yan et al., *Genes and Development* 11: 973–983 (1997)]. Mice lacking p27$^{KIP1}$ develop organomegaly, neurological conditions i.e., display retinal dysplasia, female sterility, and benign pituitary adenomas [Fero et al., *Cell* 85:733–744 (1996); Kiyokawa et al., *Cell* 85:721–732 (1996); Nakayama et al., *Cell* 85:707–720 (1996)]. However, mice deleted for the other CKIs examined heretofore, do not display apparent phenotypes. Mice lacking p21$^{CIP1}$ [Deng et al., *Cell* 82:675–684 (1995)] are developmentally normal and do not develop spontaneous tumors. Mice lacking p18$^{INK4c}$ develop gigantism, widespread organomegaly and pituitary adenomas by 10 months of age [Franklin et al., *Genes and Development* 12:2899–2911 (1998)], whereas mice lacking both p18$^{INK4c}$ and p27$^{KIP1}$ develop pituitary adenocarcinomas with an accelerated onset from what is seen in the p18$^{INK4c}$-double null animals (i.e., animals lacking both p18$^{INK4c}$ alleles) [Franklin et al., *Genes and Development* 12:2899–2911 (1998)]. Similarly, deletion of p27$^{KIP1}$ and p57$^{KIP2}$ leads to aberrant proliferation of these cells due to inhibition of cell cycle exit and differentiation in these tissues. In wild type mice, both p27$^{KIP1}$ and p57$^{KIP2}$ are expressed in the lens fiber cells and in placental trophoblasts, [Zhang et al., *Genes and Development* 12:3162–3167 (1998)].

Development of the central nervous system (CNS) requires proliferation of neuronal and glial cell precursors followed by their subsequent differentiation in a highly coordinated manner. However, despite the obvious need for replacement of neuronal cells in cases of neural injuries and diseases, to date, no such cell source is available. Therefore, there is presently a need for methodology that can provide an avenue for stimulating the growth of neuronal populations. Furthermore, there are relatively few if any animal models for diseases that include symptoms such as bradykinesia. Therefore, there is a need for animal models for this and other neurological maladies and disorders.

The citation of any reference herein should not be construed as an admission that such reference is available as "Prior Art" to the instant application.

SUMMARY OF THE INVENTION

The present invention provides non-human animals that have been manipulated to be missing all or essentially all of an activity of one or more specific gene/allele product(s). In a preferred embodiment of this type the non-human animal has been manipulated so as not to express functional p19$^{INK4d}$ and p27$^{KIP1}$ proteins. Preferably the non-human animal is a mammal. In addition, the present invention provides cells, preferably animal cells, and more preferably mammalian cells that have been manipulated to be missing all or essentially all of an activity of the p19$^{INK4d}$ protein, and to be missing all or essentially all of an activity of the p27$^{KIP1}$ protein. In a particular embodiment the mammalian cell is a human cell.

The present invention also provides methods of making and using these cells and non-human animals. The present invention further provides methodology for stimulating growth of cells that do not generally proliferate, such as neuronal populations. These neuronal populations can be employed to replenish those lost due to degenerative diseases such as Alzheimer's disease or Parkinson's disease, or alternatively lost through catastrophic insults such as during strokes or traumatic injury such as spinal chord injuries.

In still another aspect of the present invention the cells and non-human animals of the present invention can be used to identify potential modulators of cell growth, and more particularly neuronal growth. These modulators are also part of the present invention. Such modulators can also be used to treat degenerative diseases such as Alzheimer's disease or Parkinson's disease, or alternatively treat the loss of neuronal cells due to the result of a catastrophic insult such as that which occurs during a stroke or a traumatic injury such as a spinal chord injury.

The knockout animals and/or corresponding cells of the present invention can be manipulated to be incapable of expressing a functional protein from one or more specified alleles and/or genes by any means known in the art. For example, a knockout animal and/or corresponding cell can be manipulated to comprise a disruption in an endogenous allele(s) and/or gene(s) [e.g., one encoding the p19$^{INK4d}$ protein] thereby preventing the expression of the corresponding functional protein. Alternatively, a knockout animal and/or corresponding cell can be manipulated to comprise a dominant mutant allele. In a particular embodiment of this type nucleic acid(s) encoding one or more CDKs and/or cyclins are constructed to be under the control of a neuron-specific promoter (e.g., the enolase promoter) and are thereby overexpressed in the neuronal cell, and bind all of the free p19$^{INK4d}$ protein and/or p27$^{KIP1}$ protein.

In yet another embodiment, a knockout animal and/or corresponding cell can be treated with one or more antisense nucleic acids for one or more specific gene(s) thereby inhibiting the expression of the specific gene(s). In still another embodiment the gene(s) encoding the specific functional protein(s) can be constructed such that the expression of the protein(s) is under the control of an inducible promoter, and this expression is conditionally repressed. In still another embodiment the cell and/or non-human animal is treated with/administered inhibitory compound(s) that prevent the expression and/or activity of the p19$^{INK4d}$ protein and/or p27$^{KIP1}$ protein.

Therefore, one aspect of the present invention includes a non-human transgenic knockout animal that comprises a homozygous disruption in its endogenous p19$^{INK4d}$ gene and a heterozygous disruption in its endogenous p27$^{KIP1}$ gene, such that the homozygous disruption prevents the expression of a functional p19$^{INK4d}$ protein from either endogenous p19$^{INK4d}$ allele and the heterozygous disruption in the endogenous p27$^{KIP1}$ gene prevents the expression of a functional p27$^{KIP1}$ protein from at least one endogenous p27$^{KIP1}$ allele. The male knockout animal of this type relative to the animal with a wild type p19$^{INK4d}$ gene and p27$^{KIP1}$ gene manifests at least about a 20% to 40% reduction in testicular size. The female knockout animal of this type when mated with the corresponding male knockout animal has the phenotype of bearing male progeny that manifest at least about a 20% to 40% reduction in testicular size relative to the corresponding male having a wild type p19$^{INK4d}$ gene and p27$^{KIP1}$ gene.

The present invention further provides an isolated cell from such a non-human knockout animal. In a preferred embodiment the non-human transgenic knockout animal is a mammal. In a particular embodiment of this type, the non-human mammalian transgenic knockout animal is a knockout mouse.

The present invention further provides a non-human transgenic knockout animal that has a homozygous disruption in its endogenous p19$^{KIP1}$ gene such that the expression of a functional p19$^{INK4d}$ protein is prevented, and a homozygous disruption in its endogenous $p27^{KIP1}$ gene such that the expression of a functional $p27^{KIP1}$ protein is prevented. In a preferred embodiment of this type, the non-human transgenic knockout animal is a mammal. In a particular embodiment of this type, the non-human mammalian transgenic knockout animal is a knockout mouse.

In one embodiment a knockout animal that has a homozygous disruption in its endogenous $p19^{INK4d}$ gene and a homozygous disruption in its endogenous $p27^{KIP1}$ gene develops either or both of the following characteristics during its lifetime: (i) bradykinesia, and (ii) proprioceptive abnormalities. In a particular embodiment of this type the knockout animal exhibits one of these characteristics. In a more preferred embodiment of this type knockout the animal exhibits both of these characteristics. In a particular embodiment of this type, the knockout animal is a knockout mouse that has a life expectancy of between about 14 to about 24 days after birth.

The present invention further provides an isolated cell from a non-human knockout animal that has ahomozygous disruption in its endogenous $p19^{INK4d}$ gene and a homozygous disruption in its endogenous $p27^{KIP1}$ gene. In a particular embodiment of this type, the cell is a neuronal cell that is a member of a subpopulation of neurons. In one such embodiment the cell subpopulation is a normally dormant neuron of the hippocampus, cortex, pons, or hypothalamus. In a preferred embodiment of this type such a cell can continue to proliferate after migrating to its final positions in the brain. In still another embodiment, the present invention provides a knockout animal that has a homozygous disruption in its endogenous $p19^{INK4d}$ gene such that the expression of a functional $p19^{INK4d}$ protein is prevented, a homozygous disruption in its endogenous $p27^{KIP1}$ gene such that the expression of a functional $p27^{KIP1}$ protein is prevented and further comprises a homozygous disruption in its endogenous $p57^{KIP2}$ gene such that the expression of a functional $p57^{KIP2}$ protein is also prevented.

Another aspect of the present invention is a cell that has been manipulated to be incapable of expressing a functional $p19^{INK4d}$ protein and has been further manipulated to be incapable of expressing a functional $p27^{INK4d}$ protein from at least one endogenous $p27^{KIP1}$ allele. In a particular embodiment, the cell is a mammalian cell. In a still another embodiment, the cell has been manipulated such that it cannot express a functional $p27^{KIP1}$ protein and is incapable of expressing a functional $p19^{INK4d}$ protein from at least one endogenous $p19^{INK4d}$ allele. In a preferred embodiment the cell has been manipulated such that it can neither express a functional $p19^{INK4d}$ protein nor express a functional $p27^{KIP1}$ protein. In still another embodiment, a cell that has been manipulated such that it can neither express a functional $p19^{INK4d}$ protein nor express a functional $p27^{KIP1}$ protein, has been further manipulated to be incapable of expressing a functional $p57^{KIP2}$ protein from at least one endogenous $p57^{KIP2}$ allele. In a preferred embodiment of this type the cell has been further manipulated to be incapable of expressing a functional $p19^{INK4d}$ protein, a functional $p27^{KIP1}$ protein, and a functional $p57^{KIP1}$ protein.

The mammalian cells of the present invention can be of any cell type including a neural stem cell, a neuronal cell, a glial cell, a hemopoietic stem cell, a B lymphocyte, a T lymphocyte, a natural killer cell, a dendritic cell, a macrophage, a megakaryocyte, a keratinocyte, and a retinal cell. In a preferred embodiment, the mammalian cell is a neuronal cell.

The present invention further provides a method for selecting a potential therapeutic agent for use in the treatment of a motor condition/disorder (e.g., one in which bradykinesia is a symptom) and/or proprioceptive abnormalities. One such embodiment comprises administering a potential therapeutic agent to a non-human knockout animal that can neither express a functional $p19^{INK4d}$ protein nor express a functional $p27^{KIP1}$ protein, and measuring the response of the knockout animal to the potential therapeutic agent. The response of the knockout animal is then compared to that of an animal that expresses both functional $p19^{INK4d}$ protein and functional $p27^{KIP1}$ protein. A potential therapeutic agent is selected based on the difference in response observed between the knockout animal in the presence and absence of the potential therapeutic agent relative to that of the animal expressing both functional $p19^{INK4d}$ protein and functional $p27^{KIP1}$ protein. In a preferred embodiment the non-human transgenic knockout animal is a mammal. In a particular embodiment of this type, the non-human mammalian transgenic knockout animal is a knockout mouse.

The present invention further provides a method of proliferating neuronal cells comprising culturing a neuronal cell that can neither express a functional $p19^{INK4d}$ protein nor express a functional $p27^{KIP1}$ protein. Neuronal cells that have been proliferated and/or generated by this method are also part of the present invention. In a particular embodiment of this type, the neuronal cell is obtained from a knockout animal that can neither express a functional $p19^{INK4d}$ protein nor express a functional $p27^{KIP1}$ protein. In a preferred embodiment of this type, the neuronal cell is obtained from a knockout animal that comprises a homozygous disruption in its endogenous $p19^{INK4d}$ gene such that the expression of a functional $p19^{INK4d}$ protein is prevented, and a homozygous disruption in its endogenous $p27^{KIP1}$ gene such that the expression of a functional $p27^{KIP1}$ protein is prevented.

The present invention also includes a method of proliferating a neuronal cell comprising treating the cell with an inhibitor of the expression of the $p19^{INK4d}$ gene and an inhibitor of the expression of the $p27^{KIP1}$ gene. In another embodiment the method of proliferating a neuronal cell comprises treating the cell with an inhibitor of the $p19^{INK4d}$ protein and an inhibitor of the $p27^{KIP1}$ protein. In still another embodiment the method of proliferating a neuronal cell comprises treating the cell with an inhibitor of the expression of the $p19^{INK4d}$ gene and/or an inhibitor of the $p19^{INK4d}$ protein, and an inhibitor of the expression of the $p27^{KIP1}$ gene and/or an inhibitor of the $p27^{KIP1}$ protein.

The present invention further provides a method of treating a subject having a neurological degenerative disease such as Alzheimer's disease or Parkinson's disease, or one that has suffered a traumatic injury in which neuronal cells are damag,ed comprising implanting into the subject a neuronal cell of the present invention, which has been proliferated and/or generated by a method of the present invention into the brain of the subject. In a particular embodiment the neuronlal cell is implanted into the brain of the subject. In a preferred embodiment the neuronal cell can neither express a functional $p19^{INK4d}$ protein nor express a functional $p27^{KIP1}$ protein.

In another embodiment, the neuronal cell has been manipulated such that neither a functional $p19^{INK4d}$ protein nor a functional $p27^{KIP1}$ protein is expressed in a defined culture environment, e.g., by using a specific inducible promoter element that can be repressed in culture. However, the functional proteins are expressed after implanting the cells into a subject animal upon de-repression of the promoter in vivo (e.g., the repressor is not present in vivo). In this manner neuronal cells can be proliferated ex vivo, yet still function identically to the wild type cells i.e., express functional p19$^{INK4d}$ protein and functional p27$^{KIP1}$ protein, when implanted into the subject. Alternatively, specific inhibitors of the expression and/or activity of the functional p19$^{INK4d}$ protein and functional p27$^{KIP1}$ protein can be added to the culture medium and removed from the cells prior to implanting them into the subject.

In still another aspect of the present invention are methods of identifying a potential modulator of motor function. In one such embodiment, the method uses a non-human knockout animal that can neither express a functional p19$^{INK4d}$ protein nor express a functional p27$^{KIP1}$ protein. In a preferred embodiment the non-human knockout animal is a mammal. In a particular embodiment of this type, the non-human mammalian knockout animal is a knockout mouse. A particular embodiment of this type comprises administering a potential modulator to the non-human knockout animal and measuring the response of the knockout animal to the potential modulator. The response of the knockout animal is then compared with that of an animal having a wild type p19$^{INK4d}$ gene and a wild type p27$^{KIP1}$ gene. The potential modulator is selected based on the difference in response observed between the knockout animal in the presence and absence of the potential modulator relative to that of the animal having the wild type p19$^{INK4d}$ gene and the wild type p27$^{KIP1}$ gene. In one such embodiment the life span of the animal is determined. An increase in life span of the knockout animal is indicative that the modulator is an antagonist for the effect due to the INK4d/KIP1 double null mouse. Similarly, the decrease in the magnitude of other characteristics of the INK4d /KIP1 double null mouse such as a reduction of seizures, and or magnitude of bradykinesia, or an increase in relative propriosensing are also indicative that the modulator may be useful for motor function disorders.

The present invention provides additional methods of selecting a modulator of neuronal cell proliferation. One such embodiment comprises administering a potential modulator to a neuronal cell that has been manipulated to be missing all or essentially all of an activity of the p19$^{INK4d}$ protein. The amount of proliferation of the neuronal cell is determined and a modulator is selected when the amount of proliferation determined in the presence of the potential modulator is greater than that determined in the absence of the potential modulator. A related embodiment comprises administering a potential modulator to a neuronal cell that has been manipulated to be missing all or essentially all of an activity of the p27$^{KIP1}$ protein. The amount of proliferation of the neuronal cell is determined and a modulator is selected when the amount of proliferation determined in the presence of the potential modulator is greater than that determined in the absence of the potential modulator. In this maimer inhibitors of both proteins can be individually identified. Such inhibitors can be combined in a pharmaceutical composition along with a physiological carrier to treat neurological degenerative diseases for example.

In still another embodiment the present invention provides methods of selecting a modulator of neuronal cell proliferation using a mammalian cell that can neither express a functional p19$^{INK4d}$ protein nor express a functional p27$^{KIP1}$ protein. One such embodiment comprises administering a potential modulator to the neuronal cell and determining the amount of proliferation of the neuronal cell. A modulator of neuronal cell proliferation is selected when the amount of proliferation determined in the presence of the potential modulator is different from that determined in the absence of the potential modulator. A modulator is selected as an agonist when the amount of cellular proliferation increases whereas a modulator is selected as an antagonist when the amount of cellular proliferation decreases. Such an antagonist could be useful in preventing detrimental neural growth. All of the modulators identified by the methods of the present invention are also part of the present invention.

Accordingly, it is a principal object of the present invention to provide a non-human animal that is incapable of expressing functional p19$^{INK4d}$ and incapable of expressing functional p27$^{KIP1}$ protein.

It is a further object of the present invention to provide a non-human animal that is capable of serving as an animal model for studying a motor disorders having symptoms that include bradykiinesia and/or proprioceptive abnormalities and/or seizures.

It is a further object of the present invention to provide a mammalian cell that is capable of being used to identify agonists and antagonists of neuronal cell growth.

It is a further object of the present invention to provide methods of stimulating neuronal cell growth in cell culture.

It is a further object of the present invention to provide a method for stimulating growth of neuronal populations that are lost due to degenerative diseases, or due to traumatic injury in a subject animal.

It is a further object of the present invention to provide a method of treating subjects in need of neuronal cells by implanting into the subject a neuronal cell that has been manipulated to be incapable of expressing functional p19$^{INK4d}$ and incapable of expressing functional p27$^{KIP1}$ protein, at least during the period that the cell is cultured ex vivo.

It is a further object of the present invention to provide a method of screening drug libraries for agents that can modulate neuronal cell growth.

These and other aspects of the present invention will be better appreciated by reference to the following drawings and Detailed Description.

BRIEF DESCRIPTION OF THE DRAWINGS

FIG. 2B shows p19$^{INK4d}$ protein expression in testis from mice of indicated genotypes as determined by sequential immunoprecipitation and immunoblotting.

FIG. 4A shows a hippocampal and FIG. 4B shows a large pyramidal cortical neuron in S phase double-labeled with NFP (brown) and BrdU (red). BrdU-labeling (red) of dividing cells in early telophase in the ca 1 region of the hippocampus (FIG. 4C) and in layer V of the cerebral cortex (FIG. 4D) black arrows). FIG. 4E shows HH3-stained cells in the cal region of the hippocampus. Representative cells in M phase (black arrowhead) and G2 phase (white arrowhead) are depicted. FIG. 4F shows HH3-stained cells in layer XXX of the Cortex. FIG. 4G shows TUNEL-positive cells in the hippocampus (black arrows). FIG. 4A shows Cerebral cortex organized into 6 layers (I–VI). Most of cell death in the cortex is seen in layer II of the cerebral cortex. The inset shows higher magnification of the box shown at lower power.

Scale bars: FIGS. 4A–4B: 10 $\mu$m; FIGS. 4C–4D: 16 $\mu$m; FIGS. 4E–4F:12 $\mu$m; and FIGS. 4G–4H (inset):40 $\mu$m.

DETAILED DESCRIPTION OF THE INVENTION

Figure 1:
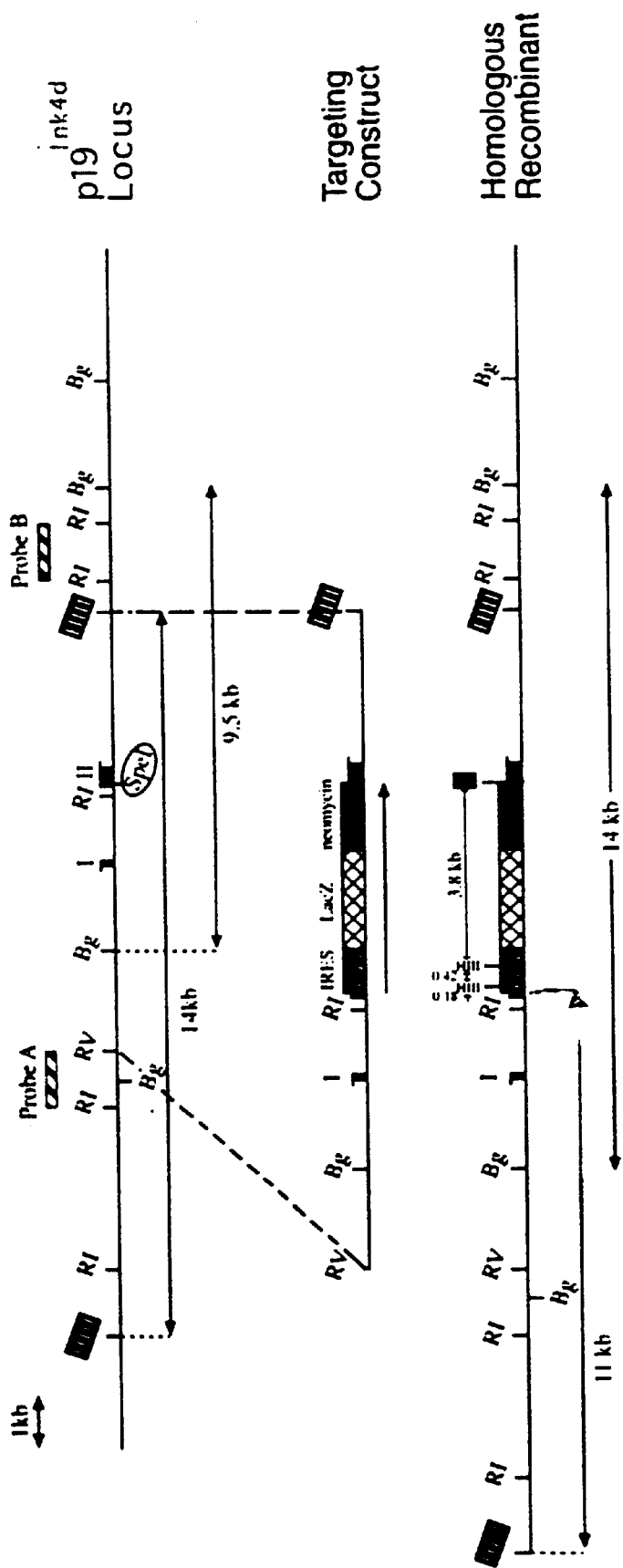
FIG. 1 shows the Mouse p19$^{INK4d}$ locus, targeting vector and targeted allele and depicts a cassette containing the LacZ gene encoding β-galactosidase fused to the neomycin gene downstream of an internal ribosomal entry site (IRES) [Mountford, and Smith, *Trends Genet* 11:179–184 (1995)] inserted into the Spel site in the second coding exon (filled in box). Only coding exons I and II were mapped.

The present invention provides non-human transgenic knockout animals that do not express a functional $p19^{INK4d}$ protein, and do not express a functional $p27^{KIP1}$ protein. Such animals can exhibit bradykinesia, proprioceptive abnormalities, seizure-like activity, and generally die 14–24 days after birth as described in the Example below. Surprisingly, subpopulations of neurons at postnatal day 18 of these knockout animals continue to proliferate after migrating to their final positions in the brain. These neuronal cells include normally dormant pyramidal cells of the hippocampus, cortex, pons, and hypothalamus. This otherwise unexpected behavior of these cells is consistent with the overlapping and sustained patterns of expression of these two CKIs, (i.e., $p19^{INK4d}$ and $p27^{KIP1}$) in post-mitotic brain cells. Although the present invention is not predicated on any particular theory, these results in toto indicate that the $p19^{INK4d}$ and $p27^{KIP1}$ proteins may be important in actively repressing neuronal proliferation, and that $p19^{INK4d}$ and $p27^{KIP1}$ cooperate to maintain differentiated neurons in a quiescent, but a potentially reversible state.

The present invention therefore affords that the deletion or inhibition of $p19^{INK4d}$ and $p27^{KIP1}$ in the adult brain can provide an avenue for stimulating novel growth of neuronal populations that are lost to degenerative diseases such as Alzheimer's disease or Parkinson's disease, or lost through catastrophic insult such as during strokes or trauma such as spinal chord injury. Therefore, the present invention provides the corresponding cells, knockout animals, and methodology for making and using these cells and knockout animals.

One aspect of the present invention is the nonhuman transgenic knockout animals that are manipulated to not express a functional $p19^{INK4d}$ protein and at least one allele from an additional gene. In a particular embodiment, the knockout animal has a double null $p19^{INK4d}$ gene, and a single null $p27^{KIP1}$ gene, resulting in the loss of the ability of the animal to express the $p19^{INK4d}$ protein and the loss of the ability of the animal to express a functional $p27^{KIP1}$ protein from at least one endogenious $p27^{KIP1}$ allele. Such a male knockout animal displays a significantt reduction in testicular size (i.e., about 20–40%) which may have an effect on its fertility. This condition may cause afflicted men profound sexual/reproductive problems. This particular knockout animal therefore is amenable for use as an experimental animal for screening potential agents affecting fertility. Analogously, cells derived from such an animal can also be used in analogous drug screens.

The present invention also provides for mammalian cells and knockout animals that in addition to carrying a double null $p19^{INK4d}$ gene, carry another single null or double null gene, such as the $p19^{INK4d}$-double null, $p27^{KIP1}$-double null mice described in the Example below. The present invention also provides mammalian cells and knockout animals that carry a single null $p_{19}^{INK4d}$ gene and another single null or double null gene, such as a $p19^{INK4}$d-single null, $p27^{KIP1}$-double null animal. Furthermore, animals that have multiple single and double null genes, are also provided by the present invention such as a $p19^{INK4d}$-double null, $p27^{KIPI}$-double null and $p57^{KIP2}$-double null mouse.

The present invention further provides cells, e.g., neuronal cells, from the knockout animals of the present invention that can be isolated and grown by the methods exemplified below. Such neuronal cells that can be isolated from a $p19^{INK4d}$-double null, $p27^{KIP1}$-double null mouse are described in the Example below. These neuronal cells can be used in treating Parkinson's disease for example. Similarly the present invention provides isolated cells including hematopoietic cells (B and T cells, macrophages, megakaryocytes), and keratinocytes from animals that are $p19^{INK4d}$-double null/$p27^{KIP1}$ single null and from animals that are $p19^{INK4d}$-double null/$p27^{KIP1}$-double null. Methods for isolating representative cells are also included herein.

Since $p27^{KIP1}$ single null animals develop tumors when challenged by gamma irradiation or when treated with chemicals such as DMBA that cause DNA breaks, the p27 is haplo-insufficient for tumor formation. Therefore the $p19^{INK4d}$-double null/$p27^{KIPI}$-single null can develop brain tumors or other malignancies since both genes are expressed ubiquitously in adult tissues. Such mice can be used as a model system for identifying agents that can be used in treating tumors.

Therefore, if appearing herein, the following terms shall have the definitions set out below:

"Gene targeting" is a type of homologous recombination that occurs when a fragment of genomic DNA is introduced into a mammalian cell and that fragment locates and recombines with endogenous homologous sequences as exemplified in U.S. Pat. No. 5,464,764, Issued November 1995, and U.S. Pat. No: 5,777,195, Issued Jul. 7, 1998, the contents of which are hereby incorporated by reference herein in their entireties.

As used herein the term "knockout animal" is meant to broadly describe an animal that has been manipulated to be irreversibly missing all or "essentially all" of an activity of one or more specific gene/allele product(s) relative to the corresponding wild type animal. In a particular embodiment of this type, the knockout animal contains within its genome a specific gene/allele that has been inactivated by a method such as gene targeting. As used herein the term "knockout animal" can therefore include the heterozygote animal (e.g., one defective allele and one wild-type allele), a hornozygous animal (e.g., two defective alleles) or an animal having more than one gene having at least allele that has been inactivated. In a particular embodiment of the present invention, a knockout animal is a knockout mouse that has both alleles encoding the $p19^{INK4d}$ protein inactivated and both alleles encoding the p27$^{KIP1}$ protein inactivated, i.e., a INK4d/KIP1 double-null mouse.

A knockout animal that is heterozygous for a particular gene product activity has been manipulated to be missing all or "essentially all" of the activity of at least one of the particular allele products relative to the corresponding wild type animal.

As used herein a knockout animal or cell missing "essentially all" of an activity of a specific gene/allele product, is an animal or cell that has less than about 25% of the gene/allele product activity of the corresponding wild type animal or wild type cell. In a preferred embodiment the animal or cell has less than or equal to about 20% of the gene/allele product activity of the corresponding wild type animal or wild type cell respectively.

A "single null" gene is a gene that has one defective allele (i.e., corresponding to a heterozygous gene) whereas a "double null" gene is a gene that has both alleles defective (i.e., corresponding to a homozygous gene).

As used herein the term "about" is used to signify that a value is within twenty percent of the indicated value i.e., a testicular size of a male mouse that is about 30% smaller than that of a wild type mouse is between 24% and 36% smaller than that of the wild type mouse.

As used herein potential therapeutic agents and modulators can be selected on the basis of whether there is a statistical significance between test response and the normal response. Potential therapeutic agents are selected that show a statistically significant change in the characteristic measured/determined. In a particular embodiment, the normal response of the knockout animal in the absence of a therapeutic agent is characteristically different by being characteristically lower than that of wild type mice and the selected therapeutic agents act to raise the sensitivity of that characteristic.

The terms "p19$^{INK4d}$ protein", "p19$^{INK4d}$" and "INK4d gene product" are used herein interchangeably and specify a protein as described herein which is encoded by the "p19$^{INK4d}$ gene" (or "INK4d gene"). The human p19$^{INK4d}$ protein has the amino acid sequence of SEQ ID NO:2 and is encoded by a nucleic acid having the nucleotide sequence of SEQ ID NO:1. Similarly, the murine p19$^{INK4d}$ protein has the amino acid sequence of SEQ ID NO:4 and is encoded by a nucleic acid having the nucleotide sequence of SEQ ID NO:3.

The terms "p27$^{KIP1}$ protein", "p27$^{KIP1}$" and "KIP1 gene product" are used herein interchangeably and specify a protein as described herein which is encoded by the "p27$^{KIP1}$ gene" (or "KIP1 gene"). The human p27$^{KIP1}$ protein has the amino acid sequence of SEQ ID NO:6 and is encoded by a nucleic acid having the nucleotide sequence of SEQ ID NO:5. Similarly, the murine p27$^{KIP1}$ protein has the amino acid sequence of SEQ ID NO:8 and is encoded by a nucleic acid having the nucleotide sequence of SEQ ID NO:7.

CULTURING CELLS

Preparation of Mouse Embryo Fibroblasts (MEFs)

MEFs are routinely prepared from day 13.5–14.5 embryos. The isolated embryos are placed in DMEM plus 25 mM Hepes buffer (without any serum), see, Table 1. The head and internal organs of the mouse embryos are surgically removed and the carcass is then washed in PBS 3 times under a sterile hood. The washed carcass is then minced with a sterile scalpel. The minced carcass is digested with a 0.05% trypsin solution containing 0.53 mM EDTA for 20 minutes at 37° C. [Trypsin is purchased from GIBCO in powder form, and 1 mg is diluted into 20 ml of water. This generates a 10×stock solution which can then be diluted in PBS to a 1×solution.] 1 ml of trypsin is used (100 ul of 10×trypsin plus 900 ul of PBS) per embryo. The solution is shaken vigorously by hand every 3 minutes. After incubating for 20 minutes, the cell/trypsin suspension is passed through a needle (18G1/2 pink needle) 3 times to completely dissociate any left over pieces.

The trypsin is next inactivated by addition of 15 ml of MEF medium containing FCS to 1 ml of the solution. The cell suspension from one embryo (15 ml) is placed into 2 T25 flasks and incubated at 37° C. in an 8% $CO_2$ humidified chamber (Passage 1). The next day a 90–95 confluency is normally obtained. The medium is exchanged for a fresh one. When the cells are confluent, the incubation is maintained for an additional day and then split 1:3. At passage 3, the 3T9 protocol is generally started. This process consists of splitting the cells at 9×10$^5$ cells per 100 mm plate every three days.

TABLE 1

Mouse Embryo Fibroblasts

| Medium: | | Final Conc. |
|---|---|---|
| Dulbecco's Modified Eagle's Medium With 4.5 g/l glucose | | 1 liter |
| Fetal Bovine Serum | 100 ml | 10% |
| 200 mM L-Glutamine (GIBCO-Life Technologies 25030-081) | 10 ml | 2 mM |
| MEM Non-Essential Amino Acids (GIBCO-Life Technologies 11140-050) | 10 ml | 0.1 mM |
| β-Mercaptoethanol (GIBCO-Life Technologies 21985-023) | 1 ml | 55 µM |
| Gentamycin (GIBCO-LIFE Technologies 15710-015) | 1 ml | 10 µg/ml |

Growing B or T Lymphocytes:

The protocols provided below can be used for culturing lymphocytes from murine spleen, thymus or bone marrow. When the cells are resuspended in RPMI, 1×10$^7$ cells/ml are added in 24 wells. 1 ml of medium containing IL-2 (200 U/ml) or Con A (40 ug/ml) is added to the 1 ml cell suspension in the well. IL-2 and Con A are used to select for T cells, or 1 ug/ml LPS is used to select for B cells.

Culturing Lymphocytes from Murine Bone Marrow: RPMI-1640 Medium is used for Cell Culture. RPMI-1640 Medium contains: RPMI-1640; 10% FBS; 2 mM glutamine (100×); 55 µM 2-mercaptoethanol (1000×); and penicillin/streptomycin (100×). Hank's Balanced Salt Solution (HBSS) containing HBSS (1×) and BSA (0.7%) is used for washing cells. Generally young mice (6–8 weeks old) are used. It is important to get lymphocytes into single cell suspension quickly in order to get the cells into the favorable environment for tissue culture. Prior to culturing, the cells are kept on ice and the medium is kept cold.

The following steps are performed in an ARC Hood: 15 ml Falcon tubes are prepared on ice with ~5 ml RPMI medium for each set of mouse legs (or leg pairs) to be extracted. The mice are killed with $CO_2$. The mice are then bled by cutting under the arm into the underlying blood vessels. The blood is allowed to drain onto a paper towel for about 30 seconds. The skin is pealed off the legs usilng forceps. As much of the muscle is cut away as possible, as are the feet. Both legs are then cut at the hip and transferred to a Falcon tube on ice. Cell strainers are placed on top of the 50 ml Falcon tubes for the preparation of the bone marrow from each set of mouse legs (or leg pairs). Sterile Petri dishes (100 mm) are prepared with 25 ml RPMI medium to collect the bone marrow. A second dish is used to collect legs. Sterile scissors and forceps are maintained in ethanol prior to use. The leg is cut at the knee and a 23 G needle/5 ml syringe is used to flush out bone marrow onto the first Petri dish. The medium is used as a reservoir for flushing. Care is taken to ensure that the needle goes into the top of bone at the red hole:—femur (at the hip); and -tibia (at the knee). The medium is checked to be sure that the bone marrow has been released and the bone is checked to ensure all the marrow is removed. The medium, now full of cells, is transferred to a 50 ml Falcon tube through a strainer and the remaining chunks are pushed through with a 5 ml syringe plunger. The cells are then spun at 400 G (1390 RPM), at 4° C. for 5 minutes. The medium is then removed and the cells are resuspended in 20 ml RPMI medium per organ. The cells are counted using a 96 well plate (adding 60 µl Trypan Blue to the wells and 60 µl of the cells (e.g., 1:1)). The lymphocytes can be readily distinguished from red blood cells.

Culturing Lymphocytes from Murine Thymus: Up until after the bleeding of the mouse, the procedure is similar to that for culturing lymphocytes from murine bone marrow, (including the use of the hood). In the preparation of lymphocytes from the thymus, however, the thymus is isolated. After the bleeding of the mouse, the skin of the mouse embryo is cut away carefully working tail to head, and then the underlying membrane is cut to expose the organs. The thymus is removed and placed in a Falcon tube on ice. 50 ml falcon tubes are prepared with Cell Strainers on top for each organ (or organ pair). An organ is placed into the strainer and a 5 ml syringe plunger is used to push the tissue through. The organ is next rinsed with ~10 ml HBSS (some connective tissue may remain) and the strainer is discarded. Care is taken to ensure that the strainer is tilted to allow liquid to pass through. If multiple organs are used, the cells are placed on ice prior to spinning. The cells are spun at 400 G (1390 RPM), at 4° C. for 5 minutes. The medium is discarded and the cells are resuspended in 10 mls RPMI medium per organ. The cells are passed through the strainer a second time, and then resuspended thoroughly and placed on ice.

The cells are counted using a 96 well plate (adding 60 µl Trypan Blue to the wells and 60 µl of the cells (e.g., 1:1)). It is important to distinguish the red blood cells from the lymphocytes. Red blood cells are smaller and more yellowish. Only the lymphocytes should be counted.

Culturing Lymphocytes from Murine Spleen: RPMI-1640 Medium is used for Cell Culture. RPMI-1640 Medium contains: RPMI-1640; 10% FBS; 2 mM glutamine (100×); 55 µM 2-mercaptoethanol (1000×); and penicillin/streptomycin (100×). Hank's Balanced Salt Solution (HBSS) containing HBSS (1×) and BSA (0.7) is used for washing cells. Generally young mice (6–8 weeks old) are used. Gey's Solution is used to lyse the red blood cells. Gey's solution contains: 4.15 g $NH_4Cl$ (155 mM) and 0.5 g $KHCO_3$; that is diluted to 500 ml with water. The solution is passed through a sterile filter and stored at 4° C. Generally young mice (6–8 weeks old) are used. It is important to get lymphocytes into single cell suspension quickly in order to get the cells into the favorable environment of tissue culture. Prior to culturing, the cells are kept on ice and the medium is kept cold.

Protocol in ARC Hood: 15 ml Falcon tubes are prepared on ice with ~5 ml RPMI medium for each organ (or organ pair) to be extracted. The mice are killed with $CO_2$. The mice are then bled by cutting under the arm into the underlying blood vessels. The blood is allowed to drain onto a paper towel for about 30 seconds. The spleen is removed and placed in a Falcon tube on ice. 50 ml falcon tubes are prepared with Cell Strainers on top for each organ. An organ is placed into the strainer and a 5 ml syringe plunger is used to push the tissue through. The organ is next rinsed with ~10 ml HBSS (some connective tissue may remain) and the strainer is discarded. Care is taken to ensure that the strainer is tilted to allow liquid to pass through. If multiple organs are used, the cells are placed on ice prior to spinning. The cells are spun at 400 G (1390 RPM), at 4° C. for 5 minutes. The medium is discarded and the cells are resuspended in 1 ml HBSS medium per organ. 3 mls of Gey's Solution is added per organ for 5 minutes to lyse the red blood cells. 10 mls of HBSS medium is added to spleen suspension and the cells are spun again at 400 G (1390 RPM), at 4° C. for 5 minutes. The cells are resuspended in 10 mls RPMI medium per organ. The cells are counted using a 96 well plate (adding 60 µl Trypan Blue to the wells and 60 µl of the cells (e.g., 1:1)). Since the Gey's Solution lyses all of the red blood cells, only lymphocytes remain for counting.

Culturing Pro B Cells from Murine Bone Marrow

The protocol is similar to that for culturing lymphocytes from Murine Bone Marrow, except the cells are resuspended in RPMI (5% FCS) and plated at a density of $2\times10^7$ in 15 ml on T220-29 irradiated feeder (NIH-3T3 over expressing IL-7; $3\times10^6$ cells/10 cm plate, irradiation 3000 rads).

The NIH-3T3 cells [T220-29 irradiated feeder] contain IL-7 in a psrαtkneo vector. $3\times10^6$ of the cells are irradiated at 3000 rads to prevent overgrowth. The cells are then grown in DMEM plus 10% Fetal Calf Serum (FCS), are trypsinized, and then resuspended (10–20 mts) in a 50 ml tube. The cells are irradiated for 4.5 minutes without attenuation (3000 rads), and then pelleted. The pelleted cells, (approximately $3\times10^6$/ml), are placed in freezer medium and frozen and stored in a controlled rate freezer (e.g., $0.5\times10^6$ to $1.5\times10^6$ cells per 6 cm—which is confluent).

The day before harvesting the marrow, the stored cell aliquots are thawed one per 10 cm dish,and incubated overnight. The next day the cells are attached and are at confluence. The desired density is: 6 cm, ⅓ surface area, 6 well, ⅑ surface area.

The marrow is then plated, $2\times10^7$, and treated with GEY's solution (see above) for 10 minutes (resulting in hypotonic ammonium chloride lysis of red blood cells). An excess of HBSS+10% FCS is then added, and the cells are spun down in a light spin. The supernatant is removed, and the cells are resuspend in culture medium (W/W RPMI+5 FCS+1% Pen Strep, 1% L-Glutamine, and 50 µM β-mercaptoethanol).

$2\times10^7$ cells (about one-half mouse) are then seeded in 15 ml of medium ($1.5\times10^6$/ml) at 37° C., 10% $CO_2$. Two days later 5–6 ml of medium is added per dish. After 4–5 days any non-adherent pellet is removed via aspiration, and the cells are resuspended in 20 ml of fresh medium. At day 7, 95% of the cells are B220+, (about $40$–$50\times10^6$ cells). The cells die at about 12–14 days in culture.

Macrophage Preparation from Mouse Bone Marrow

The femurs and tibias are removed from a mouse and the ends are cut off. The bone marrows are from the bones with a 22-gauge needle with ice-cold DMEM. The bone marrows are then collected from all 4 bones, spun down. The pelleted bone marrows are resuspended in fresh ice-cold DMEM using a 22-gauge needle. The bone marrows are spun down again, resuspended in 20 ml medium and placed into a 75 flask overnight.

The next day, the fibroblast should have adhered, and the supernatant centrifuged. The pellet is placed into 20 ml of fresh medium in a fresh flask and left for two days. After two days, a lot of macrophages have adhered and are discarded. The remaining macrophages in the supernatant are counted and then plated in 100 mm dishes in fresh medium, e.g. $1\times10^6$ cells/dish for rapid use in proliferation studies. The Bone Marrow Macrophages Medium contains: DMEM plus 15% FCS; 25% CSF-1 containing medium; 2 mM glutamine (100×); 5 uM β-mercaptoethanol (10000×) and penicillin/streptomycin.

Isolation of Megakaryocytes from Bone Marrow: (a serum-free suspension culture system)

Marrow cells are suspended in IMDM with 1% Nutridoma. $1\times10^6$ marrow cells per ml are plated in IMDM with: 1% Nutridoma-SP; 10 ng/ml of recombinant murine thrombopoietin; 2 mM 1-glutamine; 100 U penicillin; and 100 µg/ml streptomycin sulfate.

The addition of 20 ng/ml of IL-3 will increase the number of cells but is not required for all experiments. Megakaryocytes are analyzed on Day 5. A rat antimouse platelet monoclonal antibody termed 4A5 can be used to identify megakaryocytes and analyze megakaryocyte ploidy by flow cytometry after staining DNA with hypotonic propidium iodide.

Isolation and Culture of Mouse Keratinocytes:

Pregnant BALB/c mice can be purchased from Harland Sprague Dawley. This procedure can also be used for isolation of primary rat keratinocytes. 1- to 2-day old bald neonatal mice are asphyxiated and placed in Petri dishes. They are next washed in a 1% Povidone iodine solution; and rinsed thoroughly in running tap water. This is followed by washing twice with 70% ethanol. The mice may be used immediately or, if there are large numbers of animals to process, they may be placed on ice for up to 30 minutes.

The limbs and tail of each mouse are removed first. Then a single cut of the skin from the tail to the nose is made and the entire skin is gently peeled off the body using two rat-tooth forceps. One pair of forceps is used to grasp the body, while the other is used to pull off the skin. The tissue, dermis down, is then placed onto the surface of a sterile Petri dish, which, in turn, is then placed on ice until all of the skins have been collected. Using two rat-toothed forceps, each skin is floated onto the surface (dermis down) of 2.5% trypsin in HBSS in a sterile Petri dish, which is then placed at 4° C. overnight. Note, the epidermis should not be immersed in the trypsin solution. (The HBSS solution contains: 8 g/liter NaCl; 400 mg/liter KCl; 60 mg/liter $KH_2PO_4$ monobasic; 47.86 mg/liter $Na_2HPO_4$ anhydrous; and 1 g/liter glucose anhydrous; and 350 mg/liter $NaHCO_3$.)

The treated skins are removed from the trypsin and placed epidermis down on the dry surface of a sterile Petri dish. (The epidermis tends to adhere to the plastic and the dermis can be removed by pulling off with forceps. The age of the mouse affects this; the older the mouse the harder it is to remove the dermis.) The epidermal remnants are finely minced with scissors and then mixed vigorously for 45 minutes at 37° C. in "normal" medium (MEM containing 10FCS, 100 IU/ml penicillin, 100 µg/ml streptomycin and 2–4 mM L-glutamine; 10 ml per five mouse skins) in a sterile flask containing a magnetic stirrer. The solution is then strained through four layers of sterile Nitex gauze (16xx mesh, Martin Supply). (The stratum corneum of the skins is left on the surface of the gauze while the cells pass through.) The cells are plated out at one skin equivalent per 10 ml of medium onto tissue culture plasticware or onto glass cover slips. These are then Incubated at 37° C. for 4–12 hours. Alternatively, the cells can be collected as a pellet by centrifugation (800 g for 10 minutes), resuspended in medium containing 10% DMSO and then frozen in liquid nitrogen for later use. After 4–12 hours, small groups of cells are observed on the culture plate. The cells are then transferred into a low-calcium containing medium in which the keratinocytes will proliferate. This transfer prevents stratification of the cells.

The low-calcium medium is composed of MEM (prepared without any calcium) and 10% chelated FCS (as well as normal levels of penicillin and streptomycin). The chelated serum is prepared as follows: 20 g of a resin, Chelex 100 (Bio-Rad), is used per 50 ml of serum. The resin is placed in water at 40 g/l., and the pH is adjusted to about 7.4. The resin is collected by filtration through Buchner funnel onto filter paper. The resin is added to FCS and stirred for 60 minutes. Following filtration to clarify the serum, the serum is sterilized by sequential passage through 0.45-µm filters. The approximate level of calcium in the complete medium is 0.09 mM. This compares with a level of 0.15 mM in normal medium.

Mouse keratinocytes can be maintained for up to one week in the low-calcium medium, although cell viability appears to drop after this time. There are several low-calcium, serum-free media available commercially from Clonetics and GIBCO/BRL for maintenance of keratinocytes. Keratinocytes can be kept for much longer periods in such media and in most instances will undergo several rounds of division. To induce stratification of the keratinocyte cultures, medium containing normal levels of calcium is added to the cells. It is preferable to use disposable tissue culture plasticware rather than glassware. Glassware, when needed, should be acid-washed and then autoclaved. Instruments needed for the procedures are rat-toothed forceps, sharp dissecting scissors and biopsy punches. These should be autoclaved or dipped in 95% ethanol and flamed.

Primary Neuronal Cultures

Low density primary cell cultures can be used for any population of cells that are dividing [See, Vicario-Abejon et al., *Neuron* 15:105–114 (1995)]. Embryonic day 16 hippocampus (or other CNS division, depending on site of interest) from C57BL/6J mice, for example, can be dissected and placed in a Hanks balanced salt solution (HBSS). The hippocampus can be minced to small pieces, and incubated in papain (20U/ml) with L-cysteine (1 mM), EDTA (0.5 mM), and DNAse (1000 U/mL) (Worthington Biochemical Corp., Freehold, N.J.), for 30 minutes at 37° C. A maximum of 10 hippocampi (or other brain region) in 5 mls prepared in the papain solution is effective for single cell dissociation without cell injury. A second incubation with fresh papain solution (for 30 minutes, at 37° C.) is followed by a single rinse with HBSS and then three rinses in DULBECCO media (DMEM) with 10% fetal bovine serum (FBS). The tissue is triturated in 5 mls of the above media and the cell suspension is layered over 10 mg/ml of BSA and 10 mg/ml of ovomucoid albumen. The cell suspension is spun at 1400 rpm for 8 minutes, and the pellet is resuspended in 1.0 ml of 1:1 DMEM/F12 (from GIBCO) with 10% FBS and the following supplements: 25 ug/ml insulin, 100 ug/ml transferrin, 100 uM putrescine, 30 nM sodium selenite, 50 U/ml penicillin and 50 mg/ml streptomycin. The cells can be counted using 0.4% trypan blue to indicate cell viability.

The cells are next adjusted to $1.0\times10^6$ cells/ml and plated at approximately 45,000 cells/cm² in Lab-Tek (™) permanox chamber slides, previously coated with 15 ug/ml poly-L ornithlinie (Sigma). Three to four hours after plating, the media is removed and replaced with 1:1 DMEM/F12 without serum and with the supplements described above and with 10 ng/ml basic fibroblast growth factor (bFGF, from GIBCO) with 0.1% BSA to prevent adsorption.

Identifying Auonists and Antagonists of Neuronal Proliferation

Identification of two key factors which in conjunction appear to maintain differentiated neurons in a quiescent state provides a basis for screening for agents and drugs that are capable of modulating neuronal cell growth. Thus cells and non-human animals that have been manipulated to be missing all or "essentially all" of an activity of the $p19^{INK4d}$ protein and/or the $p27^{KIP1}$ protein can be used to identify modulators (e.g., agonists or antagonists) that stimulate or inhibit the proliferation of the cells, e.g., mammalian cells such as neuronal cells, either in culture or in vivo. In a particular embodiment the cells and/or knockout animals are incapable of expressing functional $p19^{INK4d}$ protein, and/or are incapable of expressing functional $p27^{KIP1}$ protein.

For example, such modulators can be useful for treating degenerative diseases such as Alzheimer's disease or Parkinsoni's disease, or replenishing neuronal cells lost through catastrophic insult such as during strokes or trauma such as spinal chord injury. Accordingly, in addition to the use of rational design to synthesize compounds that are likely to bind the $p19^{INK4d}$ or $p27^{KIP1}$ proteins and thereby serve as potential modulators in drug screening methods, the present invention further provides alternative methods for randomly testing agents as potential modulators using high throughput screens for example, which are now standard in drug development. These potential modulators can be screened for example using wild type neuronal cells and monitoring their growth in culture by methods exemplified below.

The present invention therefore includes screens for small molecule ligands or ligand analogs and mimics, as well as screens for natural ligands that bind to and agonize or antagonize the $p19^{INK4d}$ or $p27^{KIP1}$ protein in vitro and/or in vivo.

For example, knowledge of the primary sequence of a mammalian $p19^{INK4d}$ protein and/or $p27^{KIP1}$ protein and the similarity of that sequence with proteins of known function, can provide an initial clue as to the agonists or antagonists of the protein. Identification and screening of antagonists is further facilitated by determining structural features of the mammalian $p19^{INK4d}$ protein and/or $p27^{KIP1}$ protein, e.g., using X-ray crystallography, neutron diffraction, nuclear magnetic resonance spectrometry, and other techniques for structure determination. Indeed, the three dimensional structure of $p19^{INK4d}$ and $p27^{KIP1}$ in complexes with cyclin D1/CDK6 have been determined [Brotherton et al., Nature 395:244–250 (1998), Russo et al. Nature 395:237–243 (1998)]. These techniques provide for the rational design or identification of potential agonists and antagonists. In a particular embodiment, agents including antibodies, peptides and/or small organic compounds are designed\prepared to bind to CDK4 and/or CDK6 without inhibiting the cyclin-dependent kinase activity and are then further screened for their ability to prevent CKI-dependent inhibition of the cyclin-dependent kinase. Any of a number of assays that are well known in the art for determining such cyclin-dependent kinase activity can be used in these determinations.

Agents that are selected for their ability to prevent CKI-dependent inhibition of the cyclin-dependent kinase without inhibiting the cyclin-dependent kinase activity can be further screened for their ability to alleviate systems in appropriate animal models. For example 1-methyl-4-phenyl-1,2,3,6-tetrallydropyridinie, (MPTP) produces the pathological and behavioral characteristics of Parkinsoni's disease in nonhuman primates and man [Zhang et al., Exp Neurol, 155: 140–149 (1999)]. Agents that are found to be effective in such animal models can be administered to humans to modulate neuronal growth and treat e.g., Parkinson's disease. Similar methods can be performed for identifying the ability of such agents and/or alternative agents for the treatment of Alzheimer's disease or conditions brought on by catastrophic insult such as during strokes or trauma such as spinal chord injury.

An alternative approach uses recombinant bacteriophage to produce large libraries. Using the "phage method" [Scott and Smith, 1990, Science 249:386–390 (1990); Cwirla, et al., Proc. Natl. Acad. Sci., 87:6378–6382 (1990); Devlin et al., Science, 249:404–406 (1990)], very large libraries can be constructed ($10^6$–$10^8$ chemical entities). A second approach uses primarily chemical methods, of which the Geysen method [Geysen et al., Molecular Immunology 23:709–715 (1986); Geysen et al. J. Immunologic Method 102:259–274 (1987)] and the method of Fodor et al. [Science 251:767–773 (1991)] are examples. Furka et al. [14th International Congress of Biochemistry, Volume 5, Abstract FR:013 (1988); Furka, Int. J. Peptide Protein Rep. 37:487–493 (1991)], Houghton [U.S. Pat. No. 4,631,211, issued December 1986] and Rutter et al. [U.S. Pat. No. 5,010,175, issued Apr. 23, 1991] describe methods to produce a mixture of peptides that can be tested.

In a particular embodiment of the present invention such peptides can be tested in for example neuronal cells manipulated to be missing all or essentially all of the activity of the $p19^{INK4d}$ protein or the $p27^{KIP1}$ protein. Peptides can be selected on the basis of their ability to convert a property of the cells missing only the $p19^{INK4d}$ protein activity or the $p27^{KIP1}$ protein activity to that of the $p19^{INK4d}$-double null, $p27^{KIP1}$-double null cell, e.g. the ability to proliferate. In this manner agents that individually inhibit the $p19^{INK4d}$ protein or the $p27^{KIP1}$ protein can be identified.

The effective peptides can be synthesized in large quantities for use in in vivo models such as in a mouse, and tested to see if a wild type mouse can be induced to have the properties of the $p19^{INK4d}$-double null, $p27^{KIP1}$-double null mouse described in the Example below. Peptides that are found to be effective in such animal models can be administered to humans to modulate neuronal growth and thereby treat the conditions described above. It should be emphasized that synthetic peptide production is relatively non-labor intensive, easily manufactured, quality controlled and thus, large quantities of the desired product can be produced quite cheaply. Similar combinations of mass produced synthetic peptides have been used with great success [Patarroyo, Vaccine 10:175–178 (1990)].

In a related aspect, synthetic libraries [Needels et al., Proc. Natl. Acad. Sci. USA 90:10700–4 (1993); Ohlmeyer et al., Proc. Natl. Acad. Sci. USA 90:10922–10926 (1993); Lam et al., International Patent Publication No. WO 92/00252; Kocis et al., International Pat. Publication No. WO 9428028, each of which is incorporated herein by reference in its entirety], and the like can be used as the phage libraries described above.

The potential modulators/agents can be tested for their effect to modulate cell proliferation as described in the Example below. Bromodeoxyuridine (BrdU) incorporation and/or tritiated thymidine incorporation can be used, for example, as a labeling index and as a measure of cell proliferation [Vicario-Abejon el al. Neuron 15:105–114 (1995) hereby incorporated by reference in its entirety]. For example, the test neuronal cells for example can be plated and then pulsed with BrdU for a set amount of time (e.g., 18 hours) in the presence or absence of a potential modulator/agent, prior to fixation. The cells are fixed and neutralized, and incubated with BrdU monoclonal antibody. The BrdU antibody can then be detected with a labeled secondary antibody.

Alternatively [$^3$H] thymidine is added to the cells and the cells can be grown for a set amount of time (e.g., 18 hours) in the presence or absence of a potential modulator/agent. The cells can then be washed, fixed and solubilized (e.g., 0.5 N NaOH). Aliquots of the cell extract can then be counted in a scintillation counter. Potential modulators are selected as modulators when there is a difference in the amount of BrdU or tritium determined in the presence of the potential modulator relative to in its absence.

Such screening methods can be performed independently or in conjunction with an initial in vitro screen using purified $p27^{KIP1}$ and/or $p19^{INK4d}$ proteins. In this case reagents that comprise the $p19^{INK4d}$ protein or $p27^{KIP1}$ protein can be labeled for use in the screening assays. In one embodiment, the compound may be directly labeled including as part of a fusion protein, e.g., with green fluorescent protein. In another embodiment, a labeled secondary reagent may be used to detect binding of the compound to a solid phase support containing a binding molecule of interest. Binding may be detected by in situ formation of a chromophore by an enzyme label. Suitable enzymes include, but are not limited to, alkaline phosphatase and horseradish peroxidase. Other labels for use in the invention include colored latex beads, magnetic beads, fluorescent labels (e.g., fluorescein isothiocyanate (FITC), phycoerythrin (PE), Texas red (TR), rhodamine, Lucifer Yellow, AMCA blue, free or chelated lanthanide series salts, especially $Eu^{3+}$, to name a few fluorophores), chemiluminescent molecules, radio-isotopes, or magnetic resonance imaging labels.

Neuronal proliferation also can be measured in vivo by a non-invasive method by measuring neuron density by NMR microscopy. Additionally, animals models and controls can be administered BrdU (as described in the Example below) or tritiated thymidine prior to, during, and/or after the administration of a potential modulator. After the final injection, the animals are anesthetized and/or sacrificed, and the tissues of interest are removed. These tissues can be analyzed as for BrdU incorporation, or by measuring the amount of [$^3$H] counts in cell extracts. A potential modulator/agent is selected as an agonist of cell proliferation when there is an increase in the amount of BrdU or tritium determined in the presence of the potential modulator/agent relative to in its absence. Analogously a potential modulator/agent is selected as an antagonist of cell proliferation when there is a decrease in the amount of BrdU or tritium determined in the presence of the potential modulator/agent relative to in its absence.

In another aspect of the present invention, a potential modulator for ameliorating the symptoms of bradykinesia, and/or proprioceptive abnormalities can be administered to a knockout mouse that can neither express a functional $p19^{INK4d}$ protein nor a functional $p27^{KIP1}$ protein. The knockout mouse can be monitored for motor activity at about the 12 or more days after birth using a variety of behavioral techniques exemplified in Bures et al., [in *Techniques cad Basic Experiments for the Study of Brain and Behavior*, Elsevier: Amsterdam (1976), hereby incorporated by reference in its entirety]. Generally, the changes cannot be monitored prior to postnatal day 12 because before that time the motor activities of the mouse cannot be readily monitored These animals can be tested for increased life span, seizure reduction, bradykinesia, a decrease in proprioceptive abnormalities, and changes in learning and memory in the presence and absence of the potential modulator.

Symptoms of motor activity disorders such as bradykinesia and proprioceptive abnormalities can be diagnosed by behavioral tests as mentioned above. One example consists of putting the animal on its back. If the symptoms are alleviated by a potential modulator the animal returns to its position on its legs. On the other hand, the INKd/KIP1 double null mouse cannot reestablish its upright position. Yet another example of detecting the symptom of bradykinesia is performed by determining the steps per minute a mouse takes across a flat surface marked by a paper roll or in an activity box.

Similarly, proprioceptive abnormalities can be determined by raising a INKd/KIP1 double null mouse off a surface by the tail so that none of the limbs of the mouse can touch the surface. If the symptoms are alleviated by a potential modulator the animal will balance itself by extension of its legs, i.e., splay out its legs (as the wild type, mouse does). On the other hand, the INKd/KIP1 double null mouse crosses its legs, the legs are drawn in towards the ventral surface of the abdomen.

Labels

In addition to the labels listed above, suitable labels include enzymes and proteins such as green fluorescent protein, fluorophores (e.g., fluorescence isothiocyanate (FITC), phycoerythrin (Pt), Texas red (TR), rhodamine, free or chelated lanthanide series salts, especially $Eu^3+$, to name a few fluorophores), chromophores, radioisotopes, chelating agents, dyes, colloidal gold, latex particles, ligands (e.g., biotin), and chemiluminescent agents. When a control marker is employed, the same or different labels may be used for the receptor and control marker.

In the instance where a radioactive label, such as the isotopes $^3$H, $^{14}$C, $^{32}$P, $^{35}$S, $^{36}$Cl, $^{51}$Cr, $^{57}$Co, $^{58}$Co, $^{59}$Fe, $^{90}$Y, $^{125}$I, $^{131}$I, and $^{186}$Re are used, known currently available counting procedures may be utilized. In the instance where the label is an enzyme, detection may be accomplished by any of the presently utilized colorimetric, spectrophotometric, fluorospectrophotometric, amperometric or gasometric techniques known in the art.

Direct labels are one example of labels which can be used according to the present invention. A direct label has been defined as an entity, which in its natural state, is readily visible, either to the naked eye, or with the aid of an optical filter and/or applied stimulation, e.g. ultraviolet light to promote fluorescence. Among examples of colored labels, which can be used according to the present invention, include metallic sol particles, for example, gold sol particles such as those described by Leuvering (U.S. Pat. No. 4,313,734); dye sole particles such as described by Gribnau et al. (U.S. Pat. No. 4,373,932) and May et al. (WO 88/08534); dyed latex such as described by May, siipra, Snyder (EP-A 0 280 559 and 0 281 327); or dyes encapsulated in liposomes as described by Campbell et al. (U.S. Pat. No. 4,703,017). Other direct labels include a radionucleotide, a fluorescent moiety or a luminescent moiety. In addition to these direct labeling devices, indirect labels comprising enzymes can also be used according to the present invention. Various types of enzyme linked immunoassays are well known in the art, for example, alkaline phosphatase and horseradish peroxidase, lysozyme, glucose-6-phosphate dehydrogenase, lactate dehydrogenase, urease, these and others have been discussed in detail by Eva Engvall in Enzyme Immunoassay ELISA and EMIT in *Methods in Enzymology*, 70. 419–439, 1980 and in U.S. Pat. No. 4,857,453.

Suitable enzymes include, but are not limited to, alkaline phosphatase and horseradish peroxidase. Other labels for use in the invention include magnetic beads or magnetic resonance imaging labels.

Protein and nucleic acid synthesis can be monitored by metabolic labeling. Metabolic labeling occurs in vivo or during in vitro incubation of cells that express the proteins in the presence of culture medium supplemented with a metabolic label, such as [$^{35}$S]-methionine or [$^{32}$P]-orthophosphate. In addition to metabolic (or biosynthetic) labeling with [$^{35}$S]-methionine, the invention further contemplates labeling with [$^{14}$C]-amino acids or nucleotides, and [$^{3}$H]-amino acids or nucleotides (with the tritium substituted at non-labile positions).

Antisense, Gene Targeting and Ribozymes

The present invention also extends to the preparation of antisense nucleotides and ribozymes that may be used to interfere with the expression of the mammalian p19$^{INK4d}$ protein and the p27$^{KIP1}$ protein. This approach utilizes antisense nucleic acid and ribozymes to block translation of a specific mRNA, either by masking that mRNA with an antisense nucleic acid or cleaving it with a ribozyme.

Antisense nucleic acids are DNA or RNA molecules that are complementary to at least a portion of a specific mRNA molecule [See Weintraub, *Sci. Amer.* 262:40–46 (1990); Marcus-Sekura, *Nucl. Acid Rep*, 15:5749–5763 (1987); Marcus-Sekura *Anal. Biochen.*, 172:289–295 (1988); and Brysch et al., *Cell Mol. Neurobiol.*, 14:557–568 (1994)]. Preferably, the antisense molecule employed is complementary to a substantial portion of the mRNA. In the cell, the antisense molecule hybridizes to that mRNA, forming a double stranded molecule. The cell does not translate an mRNA in this double-stranded form. Therefore, antisense nucleic acids interfere with the expression of mRNA into protein. Preferably a DNA antisense nucleic acid is employed since such an RNAIDNA duplex is a preferred substrate for RNase H. Oligomers of greater than about fifteen nucleotides and molecules that hybridize to the AUG initiation codon will be particularly efficient, though larger molecules that are essentially complementary to the entire mRNA are more likely to be effective. Antisense methods have been used to inhibit the expression of many genes in vivo [Marcus-Sekura, *Anal. Biochem.*, 172:289–295 (1988); Hambor et al., *Proc. Natl. Acad. Sci. U.S.A.* 85:4010–4014 (1988)] and in situ [Arima et al., *Antisense Nucl. Acid Drug Dev.* 8:319–327(1998); Hou et al., *Antisense Nucl. Acid Drug Dev.* 8:295–308 (1998)].

Ribozymes are RNA molecules possessing the ability to specifically cleave other single stranded RNA molecules in a manner somewhat analogous to DNA restriction endonucleases. Ribozymes were discovered from the observation that certain mRNAs have the ability to excise their own introns. By modifying the nucleotide sequence of these ribozymes, researchers have been able to engineer molecules that recognize specific nucleotide sequences in an RNA molecule and cleave it [Cech, JAMA, 260:3030–3034 (1988); Cech, *Biochem Intl*, 18:7–14 (1989)]. Because they are sequence-specific, only mRNAs with particular sequences are inactivated.

Investigators have identified two types of ribozymes, Tetrahymena-type and "hammerhead"-type [Haselhoff and Gerlach, *Nature* 334:585–591 (1988)]. Tetrahymena-type ribozymes recognize four-base sequences, while "hammerhead"-type recognize eleven- to eighteen-base sequences. The longer the recognition sequence, the more likely it is to occur exclusively in the target mRNA species. Therefore, hammerhead-type ribozymes are preferable to Tetrahymena-type ribozymes for inactivating a specific mRNA species, and eighteen base recognition sequences are preferable to shorter recognition sequences.

Knock-out technology to delete a gene is exemplified in the Example below and described in U.S. Pat. Nos. 5,464, 764, Issued Nov. 7, 1995; and 5,777,195, Issued Jul. 7, 1998 (both of which are hereby incorporated by reference herein in their entireties.)

Administration

Inhibitors of the p19$^{INK4d}$ protein and the p27$^{KIP1}$ protein, including antisense and dominant-negative mutant forms of the p19$^{INK4d}$ protein and the p27$^{KIP1}$ protein can be microinjected into the brain and neurons of a subject animal. These inhibitors can be used in the treatment of neurological degenerative diseases such as Alzheimer's disease or Parkinson's disease, or in the treatment of a traumatic injury in which neuronal cells are damaged, such as during strokes.

These inhibitors may be prepared in pharmaceutical compositions, with a suitable carrier and at a strength effective for administration to a patient having Alzheimer's disease or Parkinson's disease for example. A variety of administrative techniques may be utilized, among them parenteral techniques such as subcutaneous, intravenous and intraperitoneal injections, catheterizations and the like. Compounds, including peptides can be cross-linked to appropriate carriers that allow the crossing of the blood brain barrier and is thus amenable to intravenous and intrathecal administration. In a preferred embodiment intrathecal administration is performed. The precise doses used should be based upon the recommendations and prescription of a qualified physician or veterinarian.

Also, antibodies including both polyclonal and monoclonal antibodies, and drugs that modulate the production or activity of the p19$^{INK4d}$ and p27$^{KIP1}$ proteins may possess certain diagnostic applications and may for example, be utilized for the purpose of detecting and/or measuring conditions such as the early onset of Alzheimer's disease, in order to better treat the disorder.

The present invention further contemplates therapeutic compositions useful in practicing the therapeutic methods of this invention. A subject therapeutic composition includes, in admixture, a pharmaceutically acceptable excipient (carrier) and inhibitors to the p19$^{INK4d}$ and p27$^{KIP1}$ proteins as described herein as an active ingredient. In a preferred embodiment, the composition comprises an antigen capable of modulating the specific introduction of the inhibitors into a target cell.

The preparation of therapeutic compositions which contain the inhibitors as active ingredients is well understood in the art. Typically, such compositions are prepared as injectables, either as liquid solutions or suspensions, however, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like and combinations thereof In addition, if desired, the composition can contain minor amounts of auxiliary substances such as wetting or emulsifying agents, pH buffering agents which enhance the effectiveness of the active ingredient.

The therapeutic compositions may be administered intravenously, as by injection of a unit dose, for example. The term "unit dose" when used in reference to a therapeutic composition of the present invention refers to physically discrete units suitable as unitary dosage for humans, each unit containing a predetermined quantity of active material calculated to produce the desired therapeutic effect in association with the required diluent; i.e., carrier, or vehicle.

Cells can be reimplanted in specified regions of the CNS using a stereotaxic coordinate system such as those used in current protocols of fetal cell implantation for the treatment of Parkinson's disease [Freed et al., *New England Journal of Medicine* 327:1549–1555 (1992); Diamond et al., Archives of Neurology 51:559–563 (1994) the contents of which are hereby incorporated herein by reference in their entireties.]

The present invention may be better understood by reference to the following non-limiting Example, which is provided as exemplary of the invention. The following example is presented in order to more fully illustrate the preferred embodiments of the invention. It should in no way be construed, however, as limiting the broad scope of the invention.

EXAMPLE

Postnatal Neuronal Proliferation in INK4d-KIP1 Double Null Mice

INTRODUCTION

Development of the central nervous system (CNS) requires proliferation of neuronal and glial cell precursors followed by their subsequent differentiation in a highly coordinated manner. The timing of cell cycle exit and differentiation are regulated in part by inhibitors of cyclin-dependent kinases (CKIs) [Sherr & Roberts, *Genes Devel.* 9:11149–1163 (1995); Harper & Elledge, *Curr. Opin. Genet. Dev.* 6:56–64 (1996)]. However, the relationship between the inhibitors of cyclin-dependent kinases and neuronal and glial cell proliferation has heretofore been unknown. The results below provide data indicating the role of certain such CKIs in neuronal proliferation.

MATERIALS AND METHODS

Figure 2:
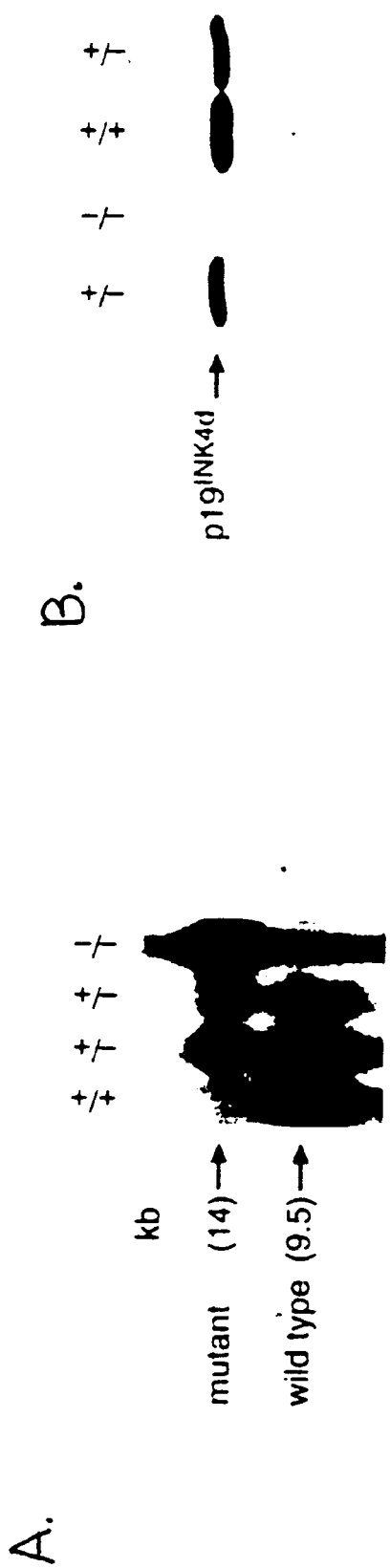
FIGS. 2A and 2B shows the Southern blotting analysis of tail DNA taken from littermates of mated INK4d hemizygotes; DNA was digested with BglII and hybridized with the 3'-end probe B (hatched box, top panel FIG. 1).

Targeting of INK4d: The genomic DNA encoding the $p19^{INK4d}$ gene was cloned from a bacteriophage library prepared from 129/SV ES cells [Van Deursen et al., *Proc. Nat. Acad. Sci. USA* 92:7576–7380 (1995)] using a full-length murine $p19^{INK4d}$ cDNA probe [(Hirai et al., *Mol. Cell. Biol.* 15: 2672–2681 (1995)]. A 14 kb EcoRV-HindIII fragment containing the two coding exons was isolated (FIG. 1, and FIGS. 2A and 2B). The INK4a targeting vector was electroporated into E14R3M4 embryonic stem cells [Fisher, et al., *Exp. Cell Res.* 182:403–414 (1989)]. Correct homologous recombination (7.6%) was determined by Southern blotting analysis of ES cell DNA. DNA was digested with BglII or HindIII, separated on an agarose gel, transferred to nitrocellulose, and hybridized with a 3'-end probe (Probe B) or a 5'-end probe (Probe A). Seven recombinant ES cell clones were injected into C57B1/6 blastocysts. After successful germline transmission of two ES clones, chimeras were bred to C57B1/6 females to generate F1 hybrids (129/SV×C57B1/6). To confirm the absence of $p19^{INK4d}$ protein expression, testis and brain were analyzed as previously described [Zindy, et al., *Cell Growth & Differ* 8:1139–1150 (1997)]. Deletion of the Kip1 gene was determined on tail DNA by polymerase chain reaction (PCR) as described previously [Fero et al., *Cell* 85:733–744 (1996)].

BrdU Labeling and tissue preparation: P18 mice of all possible genotypes were injected with BrdU (Sigma Chemical Co., MO) using 50 g/g body weight of a 5 mg/ml solution of BrdU in 0.007N NaOH, every 2 hours for a total time of 8 hours (5 injections). Two hours following the final injection, animals were anesthetized with 250 mg/kg of tribromoethanol (Sigma Chemical Co., MO) in 0.9NaCl in phosphate buffer at a concentration of 25 mg/ml and transcardially perfused with 0.9% saline followed by 95% ethanol:acetic acid (3:1). Brains and eyes were removed from the calvaria and postfixed overnight, dehydrated, defatted and embedded in paraffin. The material was then sectioned at 5 μm, and serial sections were collected on 6 series of Vectabond (Vecto Labs, CA) coated slides. Slides were stained with Haematoxylon as described [Luna, L.G. in American Histolabs, Inc., Gaithersburg, Md., 1992)].

Immunohistochemistry and TUNEL (Trans UTP Nicked End Labeling) assay: One out of 5 serial sections was processed for either BrdU [monoclonal anti-BrdU (1:100), DAKO Co., CA], NFP [monoclonal anti-neurofilament proteins, (1:300), Zymed, Calif] plus BrdU, or Histone H-3 [polyclonal anti-phospho-Histone H3 (1:100), Upstate Biotechnology, NY). Single labeling with anti-BrdU or anti-HH3 was detected using a mouse or rabbit ABC kit (Vector Labs., CA), respectively, using peroxidase anti-peroxidase (PAP) procedures [Boenisch, T. et al., DAKO Co., Carpinteria, Calif., 1989]. Double-labeling with NFP and BrdU was performed using the DAKO EnVision Doublestain System (DAKO Co., CA). One series of slides was processed for the TUNEL assay using the Dead End Colorimetric Detection System (Promega Co., WI).

Images: Images were captured using a Kontron Digital Camera and imported into Adobe Photoshop (Version 3.0, Adobe Systems). Any changes to contrast were applied equally to all images. Photographs were printed on a Fuji Pictography 300 printer.

RESULTS

The INK4d gene was disrupted by homologous recombination in embryonic stem (ES) cells (FIG. 1) and achieved germ line transmission of the null allele (FIG. 2A). Interbreeding of INK4d$^{+/-}$ heterozygotes yielded a normal Mendelian ratio of offspring [25.5% +/+: 54.2% +/-: 22.3% -/-; total 238 mice], so INK4d loss did not affect embryonic development or survival. Immunoblotting analysis of proteins from testis (FIG. 2B) and brain confirmed that INK4d deletion led to complete absence of $p19^{INK4d}$ expression. The loss of $p19^{INK4d}$ was not compensated by detectably increased expression of other INK4 proteins ($p16^{INK4a}$, $p15^{INK4b}$, and $p18^{INK4c}$) in E17.5 embryos or adult tissues. INK4d-double null animals manifested a 30–40% reduction in testicular size. This defect did not fully compromise male fertility. No additional marked defects were noted throughout adulthood. Embryo fibroblasts and T and B lymphocytes derived from these animals exhibited normal responses to mitogens and displayed cell surface markers characteristic of their lineages.

Because $p19^{INK4d}$ and $p27^{KIP1}$ are expressed in similar regions of the adult brain [Zindy, et al., *Cell Growth & Differ* 8:1139–1150 (1997); Lee, et al., *Proc. Natl. Acad. Sci. USA* 93: 3259–3263 (1996)], the INK4d-double null mouse was crossed with a KIP1-double null mouse [Fero et al., *Cell* 85: 733–744 (1996)]. Mating of male and female mice hemizygous for INK4d and KIP1, respectively, generated offspring of all possible genotypes in accord with Mendelian predictions that approximately 1/16 of all live births would lack both genes. At birth, the INK4d/KIP1 double-null animals appeared normal. However, from postnatal day 14 (P14) onward, they developed progressive paresis, bradykinesia, tremors, hypertonia, proprioceptive anomalies, disruption in righting reflexes, light sensitivity, and seizure-like activity. By P18, most mice exhibited Cheyne-Strokes respiration and died. Progression of neurological signs and morbidity was remarkably reproducible in INK4d/KIP1 double-null mice, although some animals died as early as P14 and a few as late as P24. This phenotype was observed for mice arising from two independently derived ES clones disrupted for INK4d crossed with one strain lacking KIP1 [Fero et al., Cell 85:733–744 (1996)]. No similar abnormalities were observed in animals of other genotypes containing at least one normal INK4d or KIP1 allele.

Figure 3:
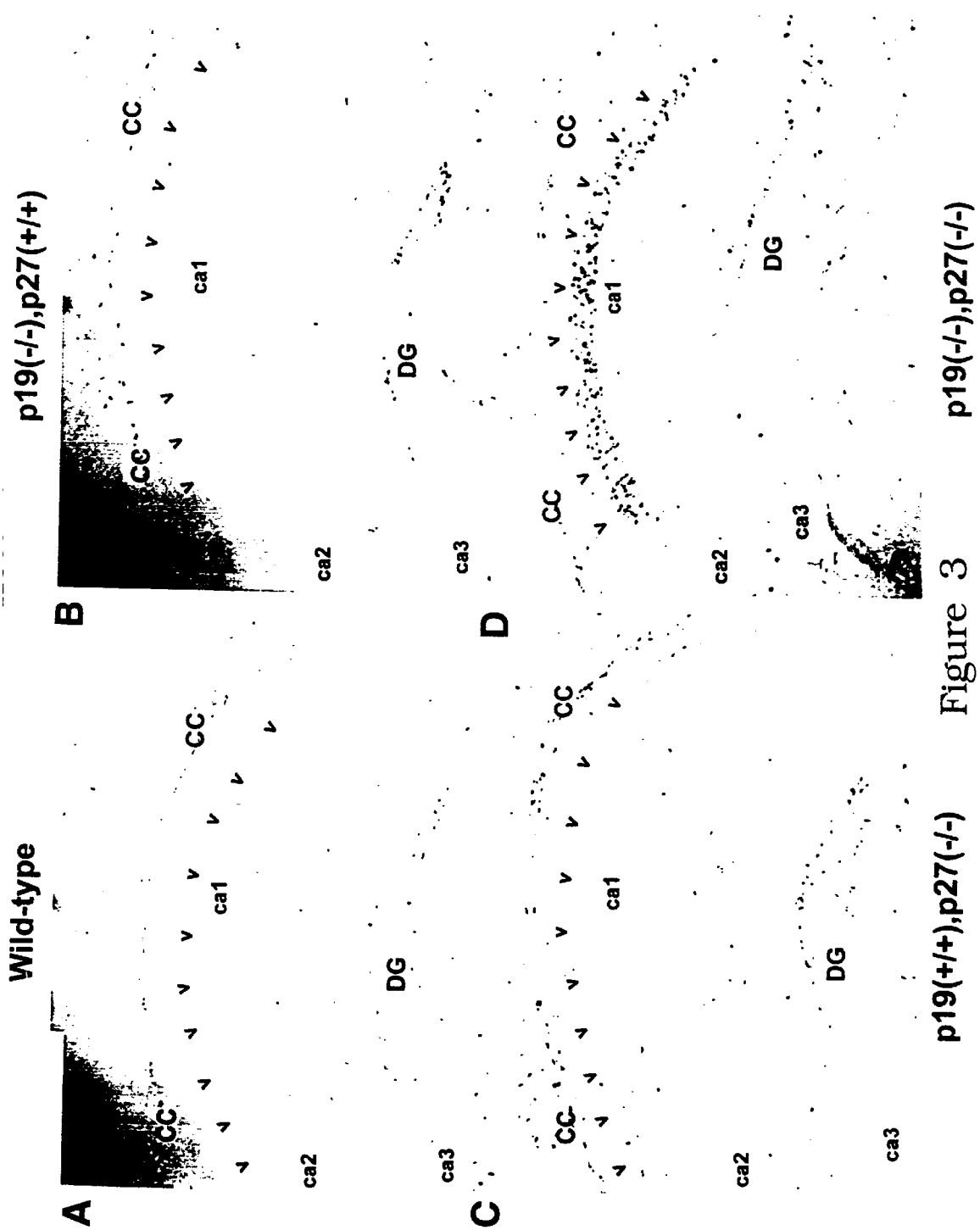
FIG. 3A–3D show BrdU labeling of hippocampus at postnatal day 18 from Wild type (FIG. 3A); INK4d-double null (FIG. 3B), KIP1-double null (FIG. 3C), and INK4d/KIP1 double-null mice (FIG. 3D). Symbols: CC, corpus callosum; DG, dentate gyrus; ca1 through ca3, corpora Ammon's sectors 1 through 3; scale bar as shown equal to 200 μm.

Enforced expression in cells of either p27$^{KIP1}$ or p19$^{INK4d}$ inhibits retinoblastoma (Rb) protein phosphorylation and entry into the DNA replicative (S) phase of the cell cycle [Sherr, & Roberts, Genes Devel. 9:1149–1163 (1995); Harper & Elledge, Curr. Opin. Genet. Dev. 6: 56–64 (1996); and Weinberg, Cell 81:323–330 (1995)]. Conversely, disruption of both genes might lead to unscheduled S phase entry and continued division in brain cells that normally express both CKIs. P18 mice were pulse-labeled with 5-bromodeoxyuridine (BrdU), which allows detection of cells in S phase [Goz, Phacrmacol Rev. 29:249 (1978)]. In wild-type animals, BrdU-labeling was absent in grey matter of the brain except, as expected, in specialized regions of the dentate gyrus (FIG. 3A), olfactory bulb, rostromedial migratory stream, and subventricular zone where some cells proliferate after birth [Thomas et al., Gila 17:1–14 (1996) and Craig, J. of Neuroscieice 16:2649–2658 (1996)]. BrdU-positive cells were also observed in the corpus callosum (FIG. 3A), which are presumed to be of glial origin [Faddis. & Vijayan, American Journal of Anatomy 183:316–322 (1988)]. In mice lacking INK4d alone, the pattern of BrdU-labeling was identical to that of wild-type animals (FIG. 3B). In KIP1-double null mice, increased glial proliferation was observed (FIG. 3C) [Casaccia-Bonnefil, et al., Genes & dev. 11:2335–2346 (1997)]. However, these mice do not exhibit frank neurological abnormalities [Fero et al., Cell 85:733–744 (1996); Nakayama et al., Cell 85:707–720 (1996); and Kiyokawa et al., Cell 85:721–732 (1996)]. Brains from INK4d/KIP1 double-null mice exhibited BrdU labeling in the corpus callosum recapitulating the same feature observed in mice lacking KiP1 alone. In contrast, the hippocampi of INK4d/KIP1 double-null mice revealed prominent BrdU-labeling in the pyramidal cell layer (FIG. 3D), a region that does not normally contain replicating cells postnatally [Stanfield & Cowan, Journal of Comparative Neurology, 185:423–459 (1979)]. BrdU labeling was also observed in layers III and V of the cerebral cortex and in other regions such as the hypothalamus, pontine nucleus, brainstem reticular formation and retina.

To examine if BrdU-positive cells were of neuronal, glial or as yet unspecified lineage, BrdU labeling was combined with staining for either a neuron-specific marker, neurofilament protein (NFP) [Lee et al., J. of Neuroscience 6:850–858 (1986)], or a glial marker, glial fibrillary acidic protein (GFAP) [Bignami. & Dahl, J. of Histochemistry & Cytochemistry 25:466–469 (1977); Meltzer et al., J. of Neuroscience 88:93–98 (1998)]. The majority of cells that incorporated BrdU also expressed NFP (FIGS. 4A–4D), whereas very few cells were double-labeled with GFAP. This clearly demonstrated that the BrdU-positive cells in the CNS of INK4d/KIP1 double-null mice were differentiated neurons. Since BrdU was pulsed for 8 hours at P18, the onset of S phase had to occur in neuronal populations that had already migrated and differentiated to their sites of residence. These events are normally completed well within the embryonic period [Stanfield. & Cowan, Journal of Comparative Neurology 185:423–459 (1979); Gardette, J fur Hirnforschung 23:415–431 (1982), and Gonzalez et al., J of Neuroscience 17:9204–9211 (1997)].

Figure 4:
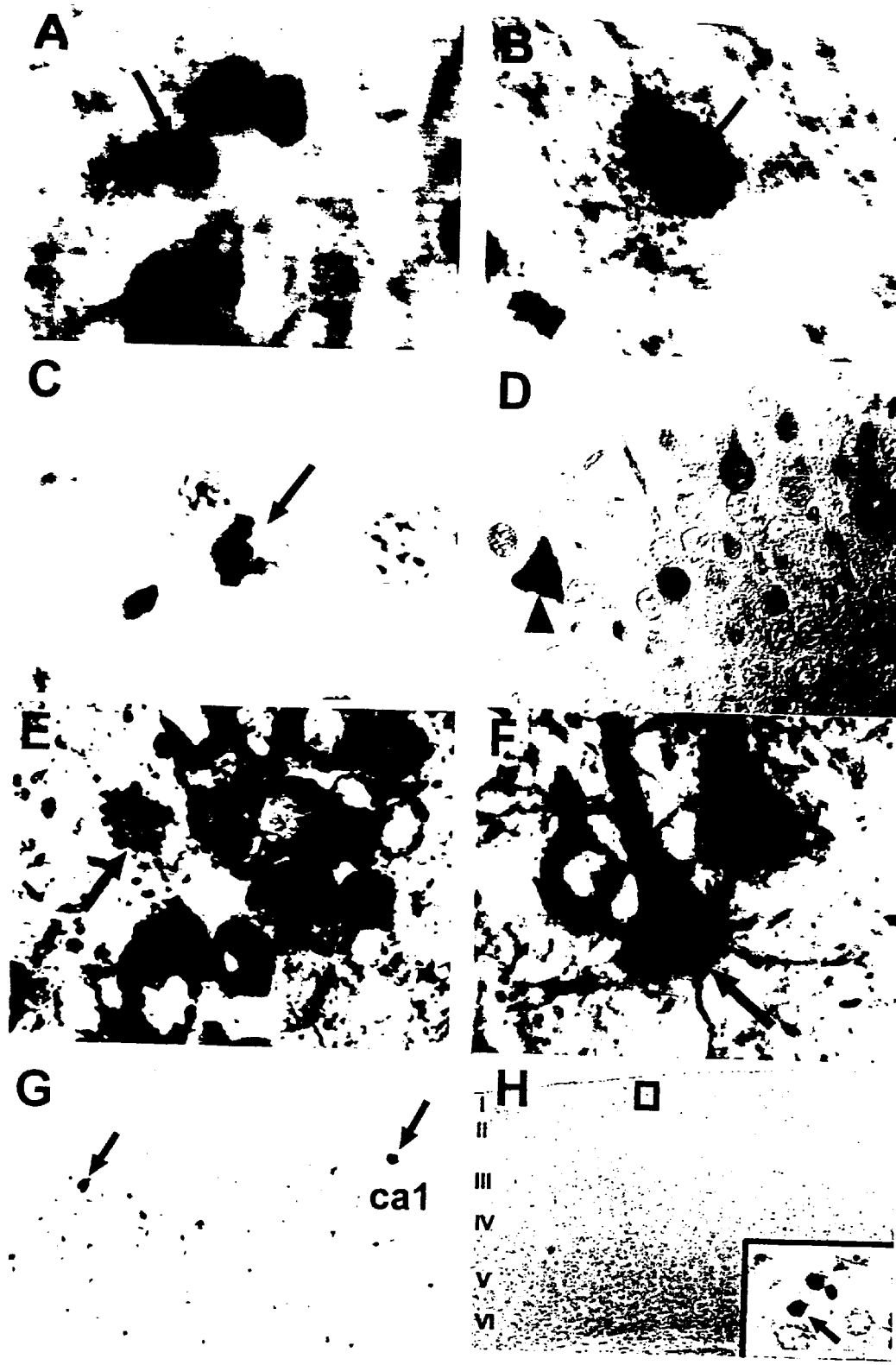
FIG. 4A–4H show markers of cell division and cell death in brains of INK4d/KIP1 double-null mice.
Figure 5:
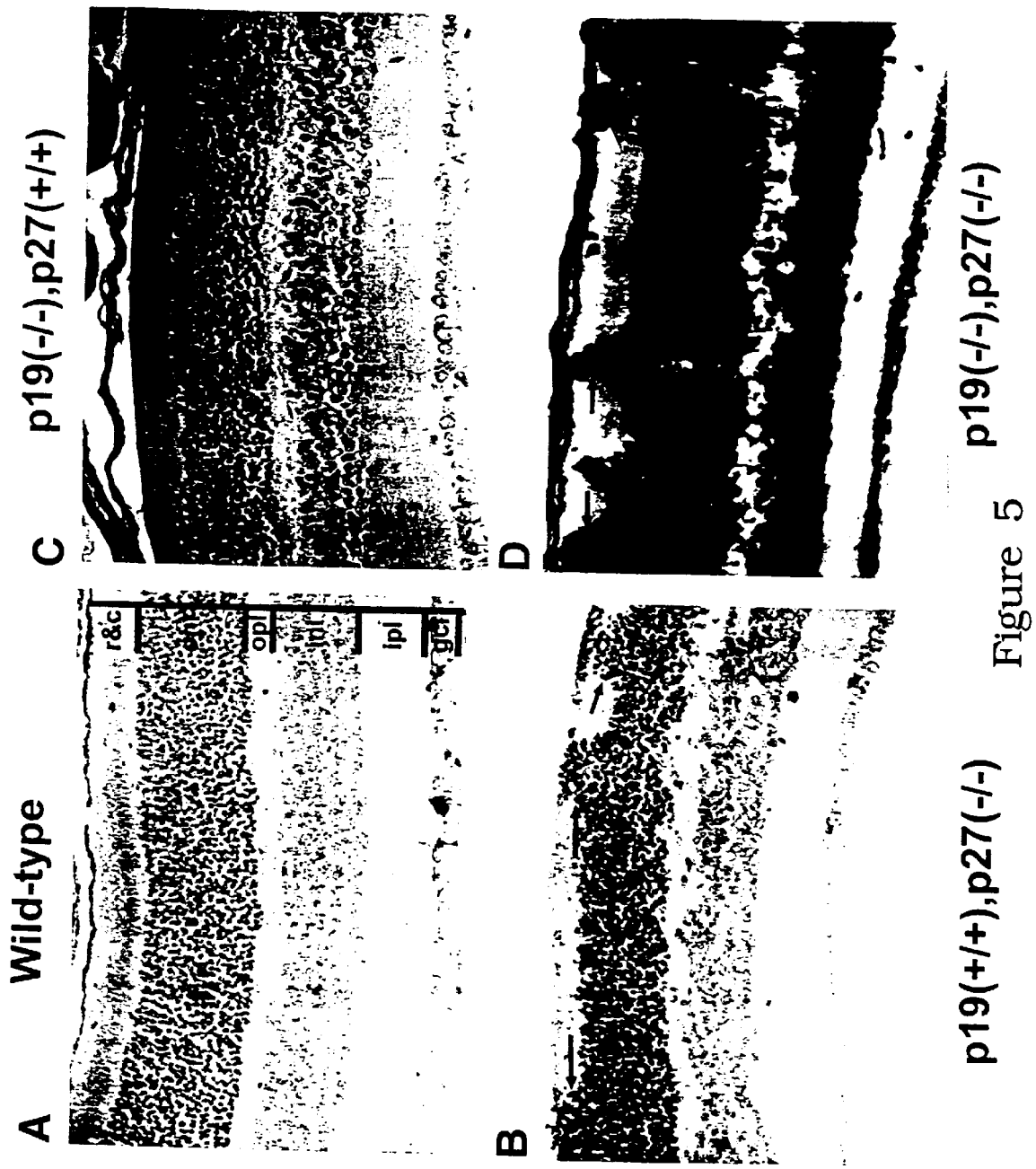
FIG. 5 depicts the morphology of the P18 retina. Retina from wild type animals (FIG. 5A); $p19^{INK4d}(-/-)$, $p27^{KIP1}$ (+/+) (FIG. 5B); $p19^{INK4d}(+/+)$ $p27^{KIP1}(-/-)$ (FIG. 5C); $p19^{INK4d}(-/-)$, $p27^{KIP1}(-/-)$ (FIG. 5D) mice. gcl, ganglion cell layer; ipl, inner plexiform layer; inl, inner nuclear layer; opl, outer plexiform layer; onl, outer nuclear layer; r&c, rod and cone photo receptor layer. Rosette of bipolar and cone cells (white arrow).

While incorporation of BrdU identified cells that entered S phase, it did not provide direct evidence that these cells were actually capable of undergoing mitosis. Therefore, histone H3 (HH3) was examined, whose expression is restricted to the G2 and M phases of the cell cycle. In G2 phase, cells expressing HH3 exhibit punctate nuclear staining which changes to a more condensed staining pattern in M phase [Hendzel et al., Cromosoma 106:348–360 (1997)]. HH3 and BrdU staining were observed in the same brain regions, particularly within the pyramidal layer of the hippocampus (FIG. 4E). Further examination of sections labeled for both BrdU and NFP revealed the presence of BrdU-positive neuronal mitotic figures (FIGS. 4C and 4D). Therefore, by use of two independent methods, BrdU-positive neurons was documented in INK4d/KIP1 double-null mice completed S phase and progressed through G2 and M phase.

Although many organs including the brains of KIP1-double null mice are enlarged after birth [(Fero et al., Cell 85:733–744 (1996); Nakayama et al., Cell 85:707–720 (1996); and Kiyokawa et al., Cell 85:721–732 (1996)], comparison of brain weight and histology did not reveal evidence of further organomegaly in INK4d/KIP1 double-null mice, and no gross morphological anomalies were noted in the CNS cytoarchitecture. Therefore, it was determined whether neuronal proliferation might be compensated by apoptosis. TUNEL assays (FIGS. 3G and 3H) together with Haematoxylin and eosin staining of serially adjacent sections, indicated that brains of INK4d/KIP1 double-null mice contained numerous pyknotic cells present in layer II of the cortex and in the outer margins of the pyramidal layer of the hippocampus. TUNEL-positive and pyknotic cells were not observed in brains from wild type animals or in those lacking INK4d or KIP1 alone. Therefore, increased cell death occurred in select neuronal populations, but these differed from those that were undergoing proliferation.

The phenotype of INK4d/KIP1 double-null mice is unique and has not been observed in mice lacking other CKIs, either alone or in combination [Fero et al., Cell 85:733–744 (1996); Nakayama et al., Cell 85:707–720 (1996); Kiyokawa et al., Cell 85:721–732 (1996); Matsuoka et al., Genes & Devel. 9:650–662 (1995); Yan et al., Genes and Development 11: 973–983 (1997); Zhang et al., Nature 387:151–158 (1997); Deng et al., Cell 82:675–684 (1995); Serrano, M. et al., Cell 85:27–37 (1996); Franklin et al., Genes and Development 12:2899–2911 (1998); and Zhang et al., Genes and Development 12:3162–3167(1998)]. Based on coexpression of p19$^{INK4d}$ and p27$^{KIP1}$ in the developed brain [Zindy et al., Cell Growth & Differ 8:1139–1150 (1997) and Lee et al., Proc. Natl. Acad. Sci. USA 93:3259–3263 (1996)] and the critical role these inhibitors may play in preventing Rb phosphorylation [Sherr and Roberts, Genes Devel. 9:1149–1163 (1995)], it was reasonable to anticipate that the phenotype of INK4d/KIP1 double-null animals might have resembled that of Rb- deficient mice. Indeed, fetal Rb-double null mice exhibit heightened neuronal proliferation followed by apoptosis, but they die due to defects in erythroid differentiation by E14.5 of embryo genesis [Lee, Nature 359:288–294(1992); Jacks et al., Nature 359:295–300(1992); and Clarke et al., Nature 359:328–330 (1992)]. In contrast, INK4d/KIP1 double-null mice survived well beyond birth and exhibited only focal neuronal apoptosis in areas of the brain that did not contain proliferating neurons. Therefore, the effects of gene loss were more highly restricted to differentiated cells that normally sustain expression of p19$^{INK4d}$ and p27$^{KIP1}$ into adulthood. The data provided herein indicates that both CKIs must cooperate to maintain differentiated neurons in a resting state after they migrate to their site of residence.

Conversely, inhibition of the function of these CKIs in the adult brain may provide an avenue for stimulating the growth of neuronal populations that are lost in degenerative diseases or through traumatic injury.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all base sizes or amino acid sizes, and all molecular weight or molecular mass values, given for nucleic acids or polypeptides are approximate, and are provided for description.

Various publications are cited herein, the disclosures of which are incorporated by reference in their entireties.

What is claimed is:

1. A knockout mouse whose genome is manipulated to comprise a homozygous disruption of both the p19$^{INK4d}$ and p27$^{KIP1}$ genes, wherein the disruption of both the p19$^{INK4d}$ and p27$^{KIP1}$ genes results in said knockout mouse exhibiting either bradykinesia, proprioceptive abnormalities or both bradykinesia and proprioceptive abnormalities.

2. A cell isolated from a knockout mouse whose genome is manipulated to comprise a homozygous disruption of both the p19$^{INK4d}$ and p27$^{KIP1}$ genes, wherein the disruption of both the p19$^{INK4d}$ and p27$^{KIP1}$ genes results in said knockout mouse exhibiting either bradykinesia, proprioceptive abnormalities or both bradykinesia and proprioceptive abnormalities.

3. The cell of claim 2, selected from the group consisting of a neuronal stem cell, a neuronal cell, a glial cell, a hemopoietic stem cell, a B lymphocyte, a T lymphocyte, a natural killer cell, a dendritic cell, a macrophage, a megakaryocyte, a keratinocyte, and a retinal cell.

4. A mouse cell whose genome is manipulated to comprise a homozygous disruption of both the p19$^{INK4d}$ and p27$^{KIP1}$ genes, wherein the disruption of both the p19$^{INK4d}$ and p27$^{KIP1}$ genes prevents expression of functional p19$^{INK4d}$ and p27$^{KIP1}$ proteins.

5. The mouse cell of claim 4, selected from the group consisting of a neuronal stem cell, a neuronal cell, a glial cell, a hemopoietic stem cell, a B lymphocyte, a T lymphocyte, a natural killer cell, a dendritic cell, a macrophage, a megakaryocyte, a keratinocyte, and a retinal cell.

6. A method of selecting an agent for treating bradykinesia comprising:

(a) measuring a symptom of bradykinesia in a knockout mouse whose genome is manipulated to comprise a homozygous disruption of both the p19$^{INK4d}$ and p27$^{KIP1}$ genes, wherein the disruption of both the p19$^{INK4d}$ and p27$^{KIP1}$ genes results in said knockout mouse exhibiting a symptom of bradykinesia;

(b) administering an agent to said mouse;

(c) measuring the symptom of bradykinesia in the mouse after administering the agent; and (d) comparing the symptom of bradykinesia in the mouse before and after administering the agent, wherein a decrease in the symptom of bradykinesia after administering the agent indicates the agent is an agent for treating bradykinesia.

7. A method of selecting an agent that modulates neuronal cell proliferation comprising:

(a) administering an agent to a first isolated mouse neuronal cell and not to a second isolated mouse neuronal cell, wherein the genome of both the first and second isolated mouse neuronal cell has been manipulated to comprise a homozyoous disruption of both the p19$^{INK4d}$ and p27$^{KIP1}$ genes, and wherein the disruption of both the p19$^{INK4d}$ and p27$^{KIP1}$ genes prevents expression of functional p19$^{INK4d}$ and p27$^{KIP1}$ proteins; and (b) determining the amount of proliferation of the first and second cell, wherein a difference in the amount of proliferation of the first cell as compared to the second cell indicates that the agent modulates neuronal cell proliferation.

* * * * *